(12) United States Patent
Arii et al.

(10) Patent No.: US 8,044,343 B2
(45) Date of Patent: Oct. 25, 2011

(54) GAS ANALYZER

(75) Inventors: Tadashi Arii, Fussa (JP); Yoshihiro Takata, Tachikawa (JP); Satoshi Otake, Ome (JP); Shigeki Matsuura, Hamamatsu (JP)

(73) Assignees: Rigaku Corporation, Akishma-Shi, Tokyo (JP); Hamamatsu Photonics K.K., Hamamatsu-Shi, Shizuoka (JP)

( * ) Notice: Subject to any disclaimer, the term of this patent is extended or adjusted under 35 U.S.C. 154(b) by 339 days.

(21) Appl. No.: 12/281,908

(22) PCT Filed: Mar. 16, 2007

(86) PCT No.: PCT/JP2007/000238
§ 371 (c)(1),
(2), (4) Date: Sep. 5, 2008

(87) PCT Pub. No.: WO2007/108211
PCT Pub. Date: Sep. 27, 2007

(65) Prior Publication Data
US 2009/0026362 A1    Jan. 29, 2009

(30) Foreign Application Priority Data

Mar. 17, 2006    (JP) .................................. 2006-073916

(51) Int. Cl.
*H01J 49/14* (2006.01)
*H01J 49/08* (2006.01)
*H01J 27/00* (2006.01)

(52) U.S. Cl. ..... 250/281; 250/286; 250/288; 250/423 R; 250/423 P; 250/427; 315/111.21; 315/111.81

(58) Field of Classification Search .................. 250/281, 250/286, 288, 427, 423 R, 423 P
See application file for complete search history.

(56) References Cited

U.S. PATENT DOCUMENTS 4,476,392 A    10/1984 Young
(Continued)

FOREIGN PATENT DOCUMENTS

JP    54-076198 A    6/1979
(Continued)

OTHER PUBLICATIONS

Notification of Transmittal of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2006/000238, Oct. 30, 2008, The International Bureau of WIPO, Geneva, CH.

(Continued)

*Primary Examiner* — Nikita Wells
(74) *Attorney, Agent, or Firm* — Buchanan Ingersoll & Rooney PC

(57) ABSTRACT

A plurality of molecule components included in a gas are to be ionized at the same time by PI method. For instance, a plurality of molecule components included in a gas generated at a certain instance are accurately analyzed in real time based on PI method. A gas analyzer is provided with a gas transfer apparatus for transferring a gas generated from a sample in a sample chamber to an analyzing chamber; an ionizer for ionizing the gas; a quadruple filter for separating ions by mass/charge ratio; and an ion detector for detecting the separated ions. The ionizer is provided with an ionizing region arranged in the vicinity of a gas exhaust of the gas transfer apparatus, and a lamp for applying light on the ionizing region. Since the lamp outputs light which has light directivity lower than that of a laser beam and travels by spreading, the gas entered the ionizing region in the ionizer receives light in a wide range, and the gas components inside are ionized at the same time.

21 Claims, 12 Drawing Sheets

U.S. PATENT DOCUMENTS

| | | | |
|---|---|---|---|
| 4,855,594 A * | 8/1989 | Kimock et al. | 250/282 |
| 5,206,594 A | 4/1993 | Zipf | |
| 5,294,797 A | 3/1994 | Frey et al. | |
| 5,629,518 A | 5/1997 | Grotheer et al. | |
| 6,329,653 B1 | 12/2001 | Syage et al. | |
| 6,967,485 B1 | 11/2005 | Hsueh et al. | |
| 7,279,680 B2 * | 10/2007 | Miller et al. | 250/288 |
| 2002/0125425 A1 | 9/2002 | Kato | |
| 2003/0020014 A1 | 1/2003 | Zimmermann et al. | |
| 2006/0043279 A1 | 3/2006 | Kudryavtsev et al. | |
| 2006/0284075 A1 * | 12/2006 | Bonne et al. | 250/288 |
| 2009/0008571 A1 * | 1/2009 | Matsuura et al. | 250/427 |
| 2009/0218482 A1 | 9/2009 | Muehlberger et al. | |

FOREIGN PATENT DOCUMENTS

| | | | |
|---|---|---|---|
| JP | 60-157017 A | 8/1985 | |
| JP | 63-55846 A | 3/1988 | |
| JP | 2-176459 A | 7/1990 | |
| JP | 3-102757 A | 4/1991 | |
| JP | 3-171544 A | 7/1991 | |
| JP | 04-152296 A | 5/1992 | |
| JP | 4-296433 A | 10/1992 | |
| JP | 5-106029 A | 4/1993 | |
| JP | 06-045092 A | 2/1994 | |
| JP | 08-030695 | 3/1996 | |
| JP | 09-068473 A | 3/1997 | |
| JP | 11-64284 A | 3/1999 | |
| JP | 2000-357488 A | 12/2000 | |
| JP | 2001-273869 A | 10/2001 | |
| JP | 2003-279543 A | 10/2003 | |
| JP | 2004-502136 A | 1/2004 | |
| JP | 2005-93152 A | 4/2005 | |
| WO | WO 2005/013341 A2 | 2/2005 | |
| WO | WO 2007/019982 A2 | 2/2007 | |

OTHER PUBLICATIONS

PCT/ISA/210.

PCT/ISA/237.

Shigeld Matsuura et al., U.S. Appl. No. 12/281,069, entitled "Ionizing Device," filed in the U.S. Patent and Trademark Office on Sep. 5, 2008.

U.S. Appl. No. 12/281,069, filed Jan. 8, 2009, Matsuura et al.

Supplementary European Search Report dated Jul. 6, 2011, issued in the corresponding European Patent Application No. 07738812.2-1232.

Japanese Notification of Reasons for Refusal issued in corresponding JP 2006-073916 on Aug. 24, 2011.

Computer translation of JP 2003-279543 downloaded from the Japanese Patent Office. Aug. 30, 2011.

* cited by examiner (a)

(b)

(a)

(b)

(a)

(b)

(c)

GAS ANALYZER

TECHNICAL FIELD

The present invention relates to a gas analyzer that ionizes gas for analysis.

BACKGROUND ART

Various gas analyzers have conventionally been known. Examples of such various gas analyzers include a differential pressure gauge that detects gas pressure, a gas densimeter that detects gas density, an infrared spectroscopic analyzer that detects vibrations of gas molecules, and a mass spectrometer that detects the mass number of ionized gas. Further, another various types of devices have been known.

Among gas analyzers, there has been a known device that performs a predetermined analysis after ionizing gas. The gas analyzer of this type may analyze gas which is present in a space or is generated from a sample. The gas analyzer that analyzes gas generated from a sample may have, at a preceding position of an ionizing unit that ionizes gas, a sample chamber for containing the sample and a gas conveyor for conveying gas generated from a sample. A mass spectrometer has been also known as one of the gas analyzers. The mass spectrometer generally includes an ionizing unit that ionizes gas, an ion-separating unit that separates the generated ions for each mass-to-charge ratio, and an ion-detecting unit that detects ion intensity.

Various methods have been conventionally known for providing an ionizing unit in a gas analyzer. For example, there have been known an Electron Ionization (EI) method, a Photo-Ionization (PI) method, and the like. The EI method is an ionization technique in which accelerated electron beams strike gaseous sample molecules to generate ions. The EI method may also be called as an Electron Impact Ionization method. The PI method is an ionization technique in which when sample molecules are irradiated with light, the molecules absorb electromagnetic wave energy thereof to cause ionization of the molecules.

A device disclosed in Patent Document 1 has been conventionally known as a gas analyzer using an ionizing unit. In this device, the EI method and the PI method are selectively performed to carry out mass spectrometry on a sample.

Patent Document 1: Japanese Patent Application Laid-Open Publication No. 2005-093152 (p. 4, FIG. 1)

DISCLOSURE OF THE INVENTION

Problems to be Solved by the Invention

In the mass spectrometer disclosed in Patent Document 1, laser light is used as a light source that achieves the PI method. As well known, laser light is artificial light having directivity, monochromatic characteristics, and high coherence. When the PI method is performed using the laser light, a local area inside the ionizing unit can be ionized, but it is difficult to sufficiently ionize the entire gas with fluidity and spreading characteristics in a short period of time. Therefore, in the conventional PI method using laser light, it is difficult to ionize a plurality of molecular components contained in the gas in a widely distributed manner at the same time for analyzing them.

For this reason, in a conventional analysis using the PI method, in order to perform a reliable gas analysis, ionization has to be performed for a long period of time while a large amount of gas is being supplied, or gas has to be separated in advance with a gas chromatograph installed at a preceding position of the ionizing unit. If gas containing a plurality of molecular components is generated from a sample and is to be ionized using the conventional PI method, it is difficult to ionize the plurality of gas molecular components at the same time. Therefore, it is also difficult to analyze the plurality of gas molecular components generated from the sample simultaneously, that is, in real-time.

The present invention has been accomplished in view of the above problems, and an object thereof is to sufficiently ionize all molecular components contained in gas at the same time, thereby allowing the plurality of the molecular components to be simultaneously analyzed based on the PI method.

Means for Solving the Problems

The gas analyzer according to the present invention is characterized by including light emitting means that emits light having an light directivity lower than that of laser light toward an ionizing region; ion separating means that separates, according to a mass-to-charge ratio, ions of a gas ionized by the light emitting means; and ion detecting means that detects the ions separated by the ion separating means. The ionizing region is a region in which light from the light emitting means can strike the gas with intensity sufficient to be able to ionize the gas.

In the gas analyzer according to the present invention, the ionizing region is set to be within an irradiation field of light emitted from the light emitting means. Within the ionizing region, photo-ionization (PI) of the gas is performed through light irradiation. The light emitting means for use in the present invention is the one that emits light having directivity lower than that of laser light. In other words, the light emitting means emits light traveling as spreading in an angle range wider than that of laser light. Examples capable of employing as such a light emitting means are a lamp, a discharge tube, or light emitter with any other structures. When the light emitting means is too close to the ionizing region, an area capable of ionizing is narrow. On the other hand, the light emitting means is too far away from the ionizing region, the light intensity in the ionizing region is too low. Therefore, the light emitting means is desirably disposed at a position where a sufficient ionization possible area can be ensured for the ionizing region and also a sufficient light intensity can be ensured.

Also, the above "ion separating means" may employ a device based on any method. Examples of applicable techniques are: (1) a quadrupole separation technique of separating ions while changing a frequency of a high-frequency voltage to be applied to a quadrupole, (2) an electromagnetic technique of separating ions by passing the ions through an electric field and a magnetic field, (3) a time-of-flight technique of applying a predetermined force to ions to cause the ions to fly to separate the ions based on a period of time until the ions reach a detector, (4) an ion trap technique. In the ion trap technique, an electrode for ion trap is added to the quadrupole for use in the quadrupole separation technique. The electrode traps, and hence retains, the separated ions for a predetermined period of time, and then sends them to a detector separately regarding the mass number. Each of the above technique separates ions according to the mass-to-charge ratio of the molecules.

According to the gas analyzer of the present invention, when a gas enters the inside of the ionizing region, the gas is irradiated with light from the light emitting means, resulting in realizing photo-ionization (PI). The generated ions are separated by the ion separating means separately regarding mass-to-charge ratio, that is, for each mass-to-charge ratio. Then, each of the separated ions is detected by the ion detecting means. In the present invention, the ionizing region is irradiated not with light having high directivity, such as laser light, but with light that travels as angularly spreading. In general, gas has a property of spreading within a short period of time, and therefore a highly directive light, such as laser light, can locally ionize the gas, but is hard to sufficiently ionize the whole gas spreading in the ionizing region within a short period of time.

On the contrary, in the present invention, the ionizing region is irradiated with a low directive light which spreads and scatters. Therefore, the entire gas dispersing in the ionizing region can be sufficiently ionized within a short period of time, thereby sufficiently ionizing all molecular components contained in the gas within a short period of time. This means, for example, that when a gas containing a plurality of molecular components is generated at some location, by conveying whole generated gas into the ionizing region within a short period of time, the conveyed gas is sufficiently ionized within a short period of time. Thus, the generated gas is subjected to processes of ionization, ion separation, and ion intensity measurement at the same time as the generation of the gas. In other words, the present invention enables to perform a so-called real-time measurement.

The gas analyzer according to the present invention includes, desirably but not necessarily as an indispensable requirement, electron generating means that generates electron for ionizing the gas. The electron generating means is desirably at least either one of electron generating means that is electrically energized to generate electrons traveling toward the ionizing region and secondary electron generating means that is irradiated with light emitted from the light emitting means to generate secondary electrons traveling toward the ionizing region. An example of the electron generating means that is electrically energized to generate electrons is a filament. Also, examples of the secondary electron generating means that is irradiated with light emitted from the light emitting means to generate secondary electrons include a filament; an electrode; a casing containing a filament, an electrode, or both; and other structures. In general, a filament is formed of a wire element, and therefore has a very small volume compared with an electrode or a casing. Therefore, capability of the filament for generating secondary electrons seems to be considerably smaller than that of the electrode or the casing.

In this aspect of the present invention, the electron generating means is a constituent element of the invention for achieving ionization based on the EI method. That is, according to this aspect of the present invention, ionization based on the PI method and ionization based on the EI method can be selectively performed. According to the EI method, electrons collide with molecular components to generate fragments (that is, cleavage components or broken pieces), thereby enabling to identify the molecular structure of the gas component type based on fragment information. On the other hand, according to the PI method, no fragment occurs, thereby clearly observing the mass number of parent ions. According to this aspect of the present invention, those advantages of the EI method and the PI method can be selected as desired.

Also, EI-method measurement data and PI-method measurement data simultaneously obtained from one generated gas can be compared for analysis. Therefore, one generated gas can be analyzed with high accuracy.

Next, both the gas analyzer according to the present invention including the electron generating means and the gas analyzer including no electron generating means desirably include: an analysis chamber containing a light discharging portion of the light emitting means, the ion separating means, and an ion receiving portion of the ion detecting means; a sample chamber where a sample is placed; and gas conveying means provided between the sample chamber and the analysis chamber to convey a gas generated from the sample to the analysis chamber. This type of gas analyzer is the one having a configuration in which the gas generated from the sample in the sample chamber is conveyed to an ionizing region for analysis.

According to the gas analyzer including the sample chamber and the gas conveying means, the gas generated from the sample is conveyed by the gas conveying means to the ionizing region in the analysis chamber. The gas is then irradiated with the light from the light emitting means in the ionizing region for photo-ionization (PI). The generated ions are separated by the ion separating means separately regarding mass-to-charge ratio, namely for each mass-to-charge ratio, ions thus separated are detected by the ion detecting means, and then ion intensity is obtained for each mass-to-charge ratio.

The gas conveyed by the gas conveying means to the ionizing region is dispersed widely in the ionizing region. According to the present invention, however, since the light emitted from the light emitting means is supplied to the ionizing region while spreading widely, a wide range of the gas dispersed in the ionizing region can be a target for ionization. Therefore, even if the amount of gas generation is small or the gas is instantaneously generated, the gas can be reliably ionized.

The gas analyzer according to the present invention may use electron-generating means or may not use electron-generating means. When electron-generating means is not employed, ionization by electron collision, that is, electron ionization, is not performed. Therefore, intensity data of ions generated only through photo-ionization (PI) can be obtained. Since no fragment ions are generated in photo-ionization (PI), the ion intensity of the very component molecules contained in the gas can be measured.

Meanwhile, in the conventional gas analyzer, the generated gas containing composite component gas cannot be separated and identified for each component gas in real-time (that is, simultaneously with gas occurrence). Therefore, the generated gas is once subjected to cold trap, each gas type is separated via a column of a gas chromatograph, and then a qualitative analysis has to be performed by using a mass spectrometer. In this case, however, a plurality of gas components contained in the generated gas cannot be caused to appear in real-time, and therefore each gas component cannot be analyzed in real-time.

Moreover, in the conventional method using a gas chromatograph, the gas may degenerate when re-heated in the column. In that case, accurate measurement results may not be obtained.

According to the gas analyzer of the present invention including the sample chamber and the gas conveying means, a plurality of produced gas contained in the gas generated from the sample can be simultaneously conveyed to the ionizing region. Then, with the conveyed gas being irradiated with widely spreading light, the plurality of produced gas can be simultaneously ionized. Then, after the ions of the plurality of gas components are separated by the ion separating means for each mass-to-charge ratio, the ion intensity of each gas component can be detected. In other words, according to the gas analyzer of the present invention equipped with the sample chamber and the gas conveying means, by measuring only single-component parent ions with photo-ionization (that is, soft ionization), the plurality of gas generated simultaneously are discriminated based on information of ions of molecules, and then identified separately. In particular, the discrimination and the identification are performed in real-time. Meanwhile, the gas generated from the sample is directly introduced to the ionizing region rather than being introduced by way of a gas chromatograph, thereby allowing the generated gas type as it is to be analyzed with high accuracy without changing its property.

Now, the gas analyzer of the present invention equipped with the sample chamber and the gas conveying means preferably includes heating means that heats the sample. The heating means can be configured by using a heating device having any structure. For example, we may employ a heater in which a heating source thereof is a heating wire or a heating member that generates heat when being electrically energized. According to this aspect of the present invention, the generated gas can be analyzed while changing the temperature of the sample by heating it or, cooling it depending on the situation. That is, the present aspect of the invention provides a thermal analyzer.

In general, generation of a gas from a sample due to a change in temperature is an instantaneous phenomenon. If light is supplied into the ionizing region while traveling as spreading according to the present invention, the entire gas generated can be sufficiently ionized, even though the generation of gas happens instantaneously. Thus, a highly reliable gas analysis can be carried out.

Now, the gas analyzer according to the present invention desirably includes electrodes capable of taking a potential state of accelerating electrons in a direction away from the ionizing region or a zero-potential state. When the electrodes are in a zero potential state, there is no occurred force that accelerates electrons being present near the ionizing region. When the electrodes are in a potential state of accelerating electrons in a direction away from the ionizing region, the electrons being present near the ionizing region are accelerated in a direction away from the ionizing region.

In the gas analyzer according to the present invention, if photo-ionization (PI) is performed by using light from the light emitting means, the parent ion corresponding to a single component gas can be measured. However, if this gas analyzer includes secondary electron generating means, when light is emitted from the light emitting means, secondary electrons are generated from that secondary electron generating means. And then, these secondary electrons affect photo-ionization to possibly make it impossible to measure only the pure parent ions. By contrast, in the present aspect of the invention, providing electrodes capable of taking a potential state of accelerating electrons in a direction away from the ionizing region or a zero-potential state can prevents secondary ions generated from the secondary electron generating means from traveling to the ionizing region. This eliminates influences of the secondary electrons on photo-ionization, so that only photo-ionization (PI) can be purely performed.

Now, the gas analyzer according to the present invention desirably includes electrodes capable of taking a potential state of accelerating electrons toward the ionizing region. If the electrodes are in a potential state of accelerating electrons toward the ionizing region, electrons which are preset near the ionizing region are accelerated toward the ionizing region. The present aspect of the invention is particularly effective to a gas analyzer equipped with secondary electron generating means. Specifically, when secondary electrons are generated from the secondary electron generating means, the electrodes can make these secondary electrons accelerate toward the ionizing region. Thus, electron ionization (EI) can be reliably performed.

Now, in the gas analyzer using the electron generating means and the electrode, these electron generating means and electrodes are desirably made of a material capable of making light pass through or have a configuration capable of making light pass through. In such a case, light from the light emitting means in the PI method can be supplied to the ionizing region in the EI method. As a result, the PI method can be realized without moving the electron generating means and the electrode both for achieving the EI method, that is, while they remain placing as it is. Thus, the ionizing unit can be constructed easily.

Now, desirably, the electron generating means is a filament formed by processing a wire element, and the paired electrodes include a combination of two electrodes selected from a mesh-shaped electrode, a spiral-shaped electrode, and a plate-shaped electrode partially provided with an opening capable of light transmission. With such a construction, light from the light emitting means for the PI-method can be reliably supplied from the outside to the inside of an EI-method device formed of electron generating means and a pair of electrodes.

Now, in the gas analyzer according to the present invention, the light emitting means preferably emits ultraviolet light or vacuum ultraviolet light. The light emitting means, such as a lamp or a discharge tube, can variously set the wavelength of emission light. Inventors of the present invention have studied through experiments which wavelength of light is appropriate for performing ionization based on the PI method. As a result, the inventors have found ultraviolet light range, vacuum ultraviolet light range, and range of soft X-ray are derivable. Here, ultraviolet light, vacuum ultraviolet light, and soft X-ray are lined up in the descending order of wavelength. Furthermore, it has been found that ultraviolet light or vacuum ultraviolet light is most suitable. In the present invention, if the wavelength of the light is set within an ultraviolet light range or a vacuum ultraviolet range, the entire gas tending to diffuse can be sufficiently ionized within a short period of time.

Now, in the gas analyzer according to the present invention, when the light emitting means is configured of a discharge tube, the gas sealed in the discharge tube is desirably a deuterium gas, a krypton gas, or an argon gas. In general, light energy emitted from the discharge tube is defined by a gas sealed in the discharge tube. Inventors of the present invention have studied through experiments which energy of light is appropriate for performing ionization based on the PI method. As a result, inventors found that a deuterium gas is desirable. It has also been found that a krypton gas and an argon gas can be used. Here, when a deuterium gas is employed, energy of light is 10.2 eV.

Now, in the gas analyzer according to the present invention including the sample chamber and the analysis chamber, it is often the case that the sample chamber is set at a high pressure inside and the analysis chamber is set at a low pressure inside. For example, the sample chamber may be set at atmospheric pressure, whilst the analysis chamber may be set at a vacuum state. In this case, the gas conveying means for use in the present invention desirably includes: an inner tube for conveying the gas; an outer tuber that covers the inner tube; and pressure adjusting means that sets a pressure of an intermediate chamber formed by the inner tube and the outer tube at a pressure lower than a pressure inside the sample chamber and higher than a pressure inside the analysis chamber.

When the sample chamber and the analysis chamber are connected together via a tube having a large diameter, it is difficult to keep a pressure difference between them with high accuracy. Moreover, when the sample chamber and the analysis chamber are connected together via a capillary (that is, a tubule), a pressure difference between the sample chamber and the analysis chamber may be sufficiently kept to a considerable degree, but it is difficult to control and send an arbitrary amount of the gas generated from the sample into the analysis chamber within a short period of time. On the contrary, according to the present invention, an outer tube with its inside being set at an intermediate pressure is provided, so that while accurately keeping different values for the pressure of the sample chamber and the pressure of the analysis chamber, a sufficient amount of gas generated from the sample in the sample chamber can be conveyed into the analysis chamber.

Furthermore, in the gas analyzer according to the present invention equipped with the sample chamber and the analysis chamber, the inside of the analysis chamber is set to be in a vacuum state. Therefore, gas ionization by the ionizing means can be performed not in atmospheric air which involves a lot of gasified molecules but under a vacuum state. In such a case, an ion-molecule reaction of gas is hard to occur, so that precise gas analysis can be performed.

Now, in the gas analyzer according to the present invention including the gas conveyor, desirably, the inner tube and the outer tube each has an orifice at the end of the sample side, and has a normal opening rather than an orifice at the end of the ionizing means side. Here, "orifice" is a small opening arranged in the tube, and yet is a sufficiently narrow hole provided in the tube and capable of changing the speed of a fluid flowing inside the tube.

Providing that an orifice is provided on the sample chamber side and a normal opening is provided on the analysis chamber side as in the case of the present aspect of the invention, most of the gas generated from the sample can be led into the inner tube, thereby supplying a sufficient amount of gas into the analysis chamber.

Now, in the gas analyzer according to the present invention in which an orifice is provided on the sample chamber side and a normal opening is provided on the analysis chamber side, a member that throttles down a cross-sectional area of a gas flow in a direction looking from a sample chamber to an analysis chamber is desirably provided near the opening on the analysis chamber side. In such a case, the generated gas can be efficiently collected to the ionizing region in the analysis chamber, so that even when generated gas is small in amount, the gas can be detected. That is, gas detection sensitivity can be increased.

Now in the gas analyzer according to the present invention, the pressure adjusting means desirably includes an exhaust pump that exhausts air from the intermediate chamber and a flow-rate adjuster provided upstream of (namely, in front of) the exhaust pump. The exhaust pump may be the one that cannot achieve a considerably high degree of vacuum and, for example, a rotary pump can be employed. According to this aspect of the invention, by exhausting the intermediate chamber by the exhaust pump, an intermediate pressure region is formed between the inner tube for conveying the gas and the sample chamber. In such a case, a sufficient amount of the gas generated from the sample in the sample chamber can be conveyed into the analysis chamber, while accurately keeping different values between the pressure of the sample chamber and the pressure of the analysis chamber.

Furthermore, in the present aspect of the invention, because a flow-rate adjuster is provided upstream of an exhaust pump, the pressure inside the intermediate chamber can be changed as desired. Therefore, the amount of introduction of the gas into the analysis chamber can be controlled. For example, if the amount of atmospheric gas flowing into through the flow-rate adjuster is increased, the pressure inside the intermediate chamber can be increased, thereby the amount of introduction of the gas into the analysis chamber can be increased.

In the present invention, gas ionization based on the PI method is performed. Depending on the aspect of the present invention, however, an ionizer achieving the EI method can be provided in addition to the ionizer achieving the PI method. In this case, ionization based on the PI method and the ionization based on the EI method can be selectively achieved. In this case, in general, the amount of ionization which is performed based on the PI method tends to be decreased compared with the amount of ionization which is performed based on the EI method. In such a cases, if the flow-rate adjuster is adjusted to increase the amount of introduction of the gas into the analysis chamber, the amount of gas to be ionized can be relatively increased.

Now, the gas analyzer according to the present invention desirably includes: the light emitting means; electron generating means that generates electrons by being electrically energized; and electrodes that accelerate the electrons; and further desirably includes control means that controls operations of the light emitting means, the electron generating means, and the electrodes. Furthermore, desirably, the control means controls a potential state of the electrodes according to a control state of the light emitting means and the electron generating means. If the potential state of the electrodes is controlled according to the control state of the light emitting means and the electron generating means, the electrodes enables to control the movement of electrons being present around the circumference of the ionizing region depending on the purpose of measurement. Here, examples of the aforesaid electrons may be thermoelectrons from the filament and secondary electrons generated due to ultraviolet irradiation.

For example, controlling of the potential state of the electrodes enables to accelerate the electrons toward the ionizing region, accelerate the electrons in a direction away from the ionizing region, and keep the electrons free from being accelerated. Acceleration of the electrons toward the ionizing region is advantageous in causing the electrons to collide with gas molecules in the ionizing region by EI. Also, acceleration of the electrons in a direction away from the ionizing region or keeping the electrons free from being accelerated is advantageous in preventing or suppressing the generation of unnecessary EI due to secondary electrons in the ionizing region while PI is performed.

Now, desirably, the gas analyzer according to the present invention includes control means that controls operations of the light emitting means, electron generating means that generates electrons by being electrically energized, and electrodes that accelerate the electrons, and the control means selectively performs a photo-ionization mode (PI mode) and an electron ionization mode (EI mode). And, desirably, (1) in the photo-ionization mode,
  the light emitting means is set to be in a light emitting state,
  the electron generating means is set to be in a potential state of not generating electrons, and
  the electrodes are set to be in a zero potential state or a potential state of accelerating the electrons in a direction away from the ionizing region, and
(2) in the electron ionization mode, desirably,
  the light emitting means is set to be in a light non-discharging state,
  the electron generating means is set to be in a potential state of generating electrons, and the paired electrodes are set to be in a potential state of accelerating the electrons toward the ionizing region.

According to this configuration, ionization based on only the PI method and ionization based on only the EI method can be selectively performed.

Here, in this aspect of the invention, desirably, the control means alternately performs the photo-ionization (PI) mode and the electron ionization (EI) mode in a time-division manner. There may be one example of time division in which one mode is first performed, and then the other mode is performed in the remaining time. There may also be another example in which one mode and the other mode may be alternately repeated each for a short time. If the photo-ionization mode and the electron ionization mode are alternately performed in a time-division manner, as in the present aspect of the invention, both of a measurement only by the PI method and a measurement only by the EI method can be performed within a short period of time.

Now, desirably, the gas analyzer according to the present invention includes control means that controls operations of the light emitting means, electron generating means that generates electrons by being electrically energized, and electrodes that accelerate the electrons, and the control means selectively performs a photo-ionization mode, an electron ionization mode, and a photo-electron ionization mode (PI+EI mode). And desirably, (1) in the photo-ionization mode,
the light emitting means is set to be in a light emitting state,
the electron generating means is set to be in a potential state where electrons are not generated, and
the paired electrodes are set to be in a zero potential state or a potential state of accelerating the electrons in a direction away from the ionizing region, (2) in the electron ionization mode,
the light emitting means is set to be in a light non-emitting state,
the electron generating means is set to be in a potential state of generating electrons, and
the paired electrodes are set to be in a potential state of accelerating the electrons toward the ionizing region, and (3) in the photo-electron ionization mode,
the light emitting means is set to be in a light discharging state,
the electron generating means is set to be in a potential state where electrons are not generated, and
the paired electrodes are set to be in a potential state of accelerating the electrons toward the ionizing region.

According to this configuration, ionization only by the PI method can be performed in the photo-ionization mode, ionization only by the EI method can be performed in the electron ionization mode, and ionization by both of the PI method and the EI method can be performed in the photo-electron ionization mode.

Also in this aspect of the present invention, preferably, the control means alternately performs the photo-ionization (PI) mode, the electron ionization (EI) mode, and the photo-electron ionization (PI+EI) mode in a time-division manner. There may be one example of time division in which one mode is first performed on one sample, another mode is then performed on another sample, and then the remaining mode is performed on still another sample. Also, three control modes may be alternately and successively repeated at predetermined time intervals while the temperature of one sample is increased according to a predetermined temperature-increasing program. As described above, if the photo-ionization (PI) mode, the electron ionization (EI) mode, and the photo-electron (PI+EI) mode are alternately performed in a time-division manner, three types of measurement, that is, a measurement only by the PI method, a measurement only by the EI mode, and a measurement by both of the PI method and the EI method, can be performed within a short period of time.

Now, desirably, the gas analyzer according to the present invention includes control means that controls operations of the light emitting means, electron generating means that generates electrons by being electrically energized, and electrodes that accelerate the electrons, and the control means selectively performs a photo-ionization mode and a photo-electron ionization mode. And, desirably, (1) in the photo-ionization mode,
the light emitting means is set to be in a light discharging state,
the electron generating means is set to be in a potential state where electrons are not generated, and
the paired electrodes are set to be in a zero potential state or a potential state of accelerating the electrons in a direction away from the ionizing region, and (2) in the photo-electron ionization mode,
the light emitting means is set to be in a light discharging state,
the electron generating means is set to be in a potential state where electrons are not generated, and
the paired electrodes are set to be in a potential state of accelerating the electrons toward the ionizing region.

According to this configuration, ionization only by the PI method can be performed in the photo-ionization mode, and ionization by both of the PI method and the EI method can be performed in the photo-electron ionization mode.

Here, also in this aspect of the present invention, desirably, the control means alternately performs the photo-ionization (PI) mode and the photo-electron ionization (PI+EI) mode in a time-division manner. As in the same manner as descried above, there may be one example of time division in which one mode is first performed, and then the other mode is performed in the remaining time. There may also be another example in which one mode and the other mode may be alternately repeated each for a short period of time. If the photo-ionization (PI) mode and the photo-electron ionization (PI+EI) mode are alternately performed in a time-division manner, as in the present aspect of the invention, both of a measurement only by the PI method and a measurement simultaneously by both of the PI method and the EI method can be performed within a short period of time.

Now, the above-described gas analyzer that performs two types of ionization, that is, ionization only by the PI method in the photo-ionization mode and ionization by both of the PI method and the EI method in the photo-electron ionization mode, desirably further includes arithmetic operating means that arithmetically produce the intensity of an ion based on an output signal of the ion detecting means. Then, the arithmetic operating means desirably performs an arithmetic operation of taking a difference of an output signal of the ion detecting means in the photo-ionization mode from an output signal of the ion detecting means in the photo-electron ionization mode.

According to this configuration, ion intensity data is measured only by the PI method and ion intensity data is measured based on simultaneous ionization by the PI method and the EI method, and then a difference between them is arithmetically operated, thereby obtaining ion intensity data only by the EI method through an arithmetic operation without an actual measurement.

Now, the gas analyzer according to the present invention desirably includes control means that controls operations of the light emitting means, electron generating means that generates electrons by being electrically energized, and electrodes that accelerate the electrons, and the control means selectively performs an electron ionization mode and a photo-electron ionization mode. And, desirably, (1) in the electron ionization mode,
the light emitting means is set to be in a light non-discharging state,
the electron generating means is set to be in a potential state of generating electrons, and
the paired electrodes are set to be in a potential state of accelerating the electrons toward the ionizing region, and (2) in the photo-electron ionization mode,
the light emitting means is set to be in a light discharging state,
the electron generating means is set to be in a potential state where electrons are not generated, and
the paired electrodes are set to be in a potential state of accelerating the electrons toward the ionizing region.

According to this configuration, ionization only by the EI method can be performed in the electron ionization mode and ionization by both of the PI method and the EI method can be performed in the photo-electron ionization mode.

Here, also in this aspect of the invention, desirably, the control means alternately performs the electron ionization (EI) mode and the photo-electron ionization (PI+EI) mode in a time-division manner. As in the same manner as descried above, there may be one example of time division in which one mode is first performed, and then the other mode is performed in the remaining time. There may also be another example in which one mode and the other mode may be alternately repeated each for a short period of time. If the photo-ionization (PI) mode and the photo-electron ionization (PI+EI) mode are alternately performed in a time-division manner, as in the present aspect of the invention, both of a measurement only by the EI method and a measurement simultaneously by both of the PI method and the EI method can be performed within a short period of time.

Now, the above-described gas analyzer that performs two types of ionization, that is, ionization only by the EI method in the photo-ionization mode, and ionization by both of the PI method and the EI method in the photo-electron ionization mode, desirably further includes arithmetic operating means that arithmetically produce an ion intensity based on an output signal of the ion detecting means. Then, the arithmetic operating means desirably performs an arithmetic operation of taking a difference of an output signal of the ion detecting means in the electron-ionization mode from an output signal of the ion detecting means in the photo-electron ionization mode.

According to this configuration, ion intensity data is measured only by the EI method and ion intensity data is measured based on simultaneous ionization by the PI method and the EI method. And then, a difference between them is arithmetically operated, thereby obtaining ion intensity data only by the PI method through an arithmetical operation without an actual measurement.

Now, the gas analyzer according to the present invention desirably includes, in addition to the light emitting means, another light emitting means that emits light having a different wavelength to the light emitting means. In this case, desirably, the gas in the ionizing region is ionized with light emitted from the light emitting means or the other light emitting means. Examples of the different light emitting means include a lamp using a deuterium gas, a lamp using a krypton gas, and a lamp using an argon gas.

According to this gas analyzer, ionization can be performed by selecting either one of light having a large amount of energy and light having a small amount of energy. Thus, the scope of selection can be expanded regarding the magnitude of the energy amount. For example, for a sample insufficiently ionized due to a small energy amount, the energy amount can be increased for sufficient ionization.

Now, the gas analyzer according to the present invention can include electrodes that generate by themselves secondary electrons by light irradiation from the light emitting means, and can have a configuration such that electron generating means that generates electrons by being electrically energized is not provided between the light emitting means and the ionizing region. In this case, desirably, the electrodes can take a potential state of accelerating the electrons in a direction away from the ionizing region, a zero potential state, or a potential state of accelerating the electrons toward the ionizing region.

According to this configuration, the PI method can be achieved by light emitted from the light emitting means, and also the EI method can be achieved by secondary electrons generated from the electrodes. That is, without using an element, such as a filament, that generates secondary electrons by being electrically energized, the EI method can be performed only by disposing electrodes serving as secondary electron generating means in a light irradiation region of the light emitting means. Thus, an ionizer and also a gas analyzer can be downsized and also reduced in cost as compared with the case where a PI-method ionizer and an EI-method ionizer are separately placed.

Here, the gas analyzer according to the present aspect of the invention can include secondary electron generating means other than the above-mentioned electrode in addition to that electrode. Examples of such secondary electron generating means can include a structure supporting the electrodes and other structures.

Effects of the Invention

According to the gas analyzer of the present invention, when a gas enters the inside of the ionizing region, the gas is irradiated with light from the light emitting means, resulting in realizing photo-ionization (PI). Then, the generated ions are separated by the ion separating means for each mass-to-charge ratio, namely separately regarding mass-to-charge ratio. And then, each of the separated ions is detected by the ion detecting means. In the present invention, the ionizing region is irradiated, not with light having high directivity, such as laser light, but with light that travels as angularly spreading. In general, gas has a property of spreading and scattering within a short period of time, and therefore a highly directive light, such as laser light, can locally ionize the gas, but is hard to sufficiently ionize the whole gas dispersing in the ionizing region within a short period of time.

On the contrary, in the present invention, the ionizing region is irradiated with a low directive light which spreads and scatters. Therefore, the entire gas dispersing in the ionizing region can be sufficiently ionized within a short period of time, thereby sufficiently ionizing all molecular components contained in the gas within a short period of time. This means, for example, that when a gas containing a plurality of molecular components is generated at some location, by conveying whole generated gas into the ionizing region within a short period of time, the conveyed gas is sufficiently ionized within a short period of time. Thus, the generated gas is subjected to processes of ionization, ion separation, and ion intensity measurement at the same time as the generation of the gas. In other words, the present invention enables to perform a so-called real-time measurement.

Figure 1:
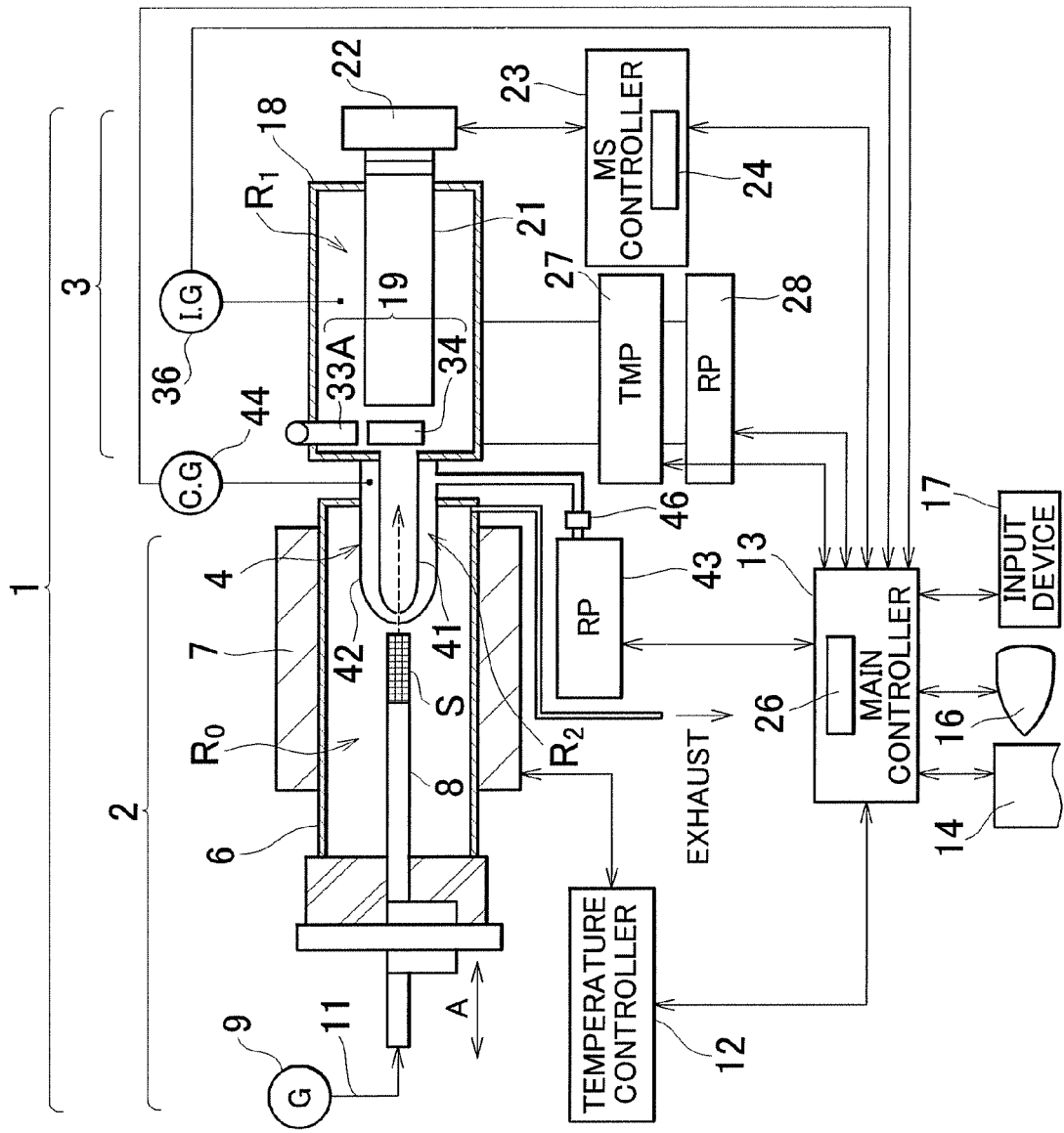
FIG. 1 is a cross-sectional view and an electric block diagram showing an embodiment of the gas analyzer according to the present invention.

EXPLANATION OF REFERENCE 1,51,71. Gas analyzer, 2. Temperature programmed desorption analyzer (gas generator), 3. Analyzer, 4. Gas conveyor, 6. Casing,
7. Heating furnace, 8. Sample tube, 9. gas supply source,
11. Piping, 18. casing, 19, 119 ionizer (ionizing means),
21. Quadrupole filter (ion separating means),
22. Ion detector (ion detecting means), 24. Electrometer,
26. Arithmetic operating unit, 29. Electrode,
31. Ion deflector, 32. Electron multiplying tube,
33A, 33B. Lump for lamp (light emitting means),
34, 134. EI device, 35. Cylinder,
37a, 37b, 137. Filament (electron generating means),
38a, 138a. External electrode (electrode, secondary electron generating means),
38b, 138b. internal electrode (electrode, secondary electron generating means),
39a, 39b, 139a, 139b. lead-in electrode, 41. Inner tube,
42. outer tube, 46. Mass flow meter (Flow-rate adjuster),
52. TG-DTA device (gas generator), 54. capillary tube (gas conveying means), 56. casing, 58. a balance beam,
59. gas supply source, 61. piping, 72. throttle member,
P. light-emitting source, Q. light-emission distribution,
R0. sample chamber, R1. analysis chamber, R3. ionizing region

BEST MODE FOR CARRYING OUT THE INVENTION

First Embodiment of the Gas Analyzer

The gas analyzer according to the present invention will be described based on embodiments thereof. It should be noted that the present invention is not limited to the following embodiment. While the present invention is described below by referring to accompanying drawings, the components may be shown in the drawings with dimensional ratios that differ from the actual ratios for the purpose of clearly showing characteristic parts thereof.

FIG. 1 shows an embodiment of the present invention, which is applied to a gas analyzer formed in combination of a temperature programmed desorption analyzer and a mass spectrometer. In FIG. 1, a gas analyzer 1 includes a temperature programmed desorption analyzer 2 serving as a gas generator and an analyzer 3 that analyzes gas. The temperature programmed desorption analyzer 2 and the analyzer 3 are connected to each other via a gas conveyor 4.

The temperature programmed desorption analyzer 2 is used as a gas generating unit for performing a thermal analysis based on a temperature programmed desorption analysis. The temperature programmed desorption analysis is an analytical method for finding a gas absorption amount or a gas absorption state from analysis of desorption process when the temperature of the surface of a solid sample on which a gas is absorbed is increased. The temperature programmed desorption analyzer 2 includes a casing 6 that forms a sample chamber R0, a heating furnace 7 serving as heating means provided around the casing 6, and a sample tube 8 inserted in the casing 6. The sample tube 8 can be removably inserted in the casing 6 as indicated by an arrow A.

The sample tube 8 supports a sample S at the forward end thereof. A gas supply source 9 is connected via a piping 11 to a rear portion of the sample tube 8. The gas supply source 9 discharges a carrier gas, for example, an inert gas, such as a helium (He) gas. The heating furnace 7 is configured of, for example, a heater having a heat-generating wire as a heating source. The heat-generating wire is electrically energized and generates heat. The heating furnace 7 generates heat according to an instruction from a temperature controller 12. When the sample chamber R0 is required to be cooled, a cooler is additionally provided to the sample chamber R0. The temperature controller 12 includes a computer, a sequencer, a dedicated circuit, or the like. A software program for increasing temperature is stored in a storage medium in the temperature controller 12.

The temperature controller 12 is activated based on an instruction from a main controller 13. The main controller 13 includes a computer, for example. A printer 14, a display 16 and an input device 17 are connected to the main controller 13 via input/output interfaces. The printer 14 may be an electrostatic transfer printer, an inkjet printer, or any other printers. The display 16 may be a CRT (Cathode-ray Tube) display, a flat-panel display (for example, liquid crystal display), or any other display devices. The input device 17 may be a keyboard-type input device, a mouse-type input device, or any other input devices.

Now, the analyzer 3 includes a casing 18 forming an analysis chamber R1, an ionizer 19 provided in the analyzer R1, a quadrupole filter 21 serving as ion separating means, an ion detector 22, and a mass spectrometry controller 23. The mass spectrometry controller 23 is connected to the main controller 13 to control the operations of each of the elements of the ionizer 19, the quadrupole filter 21, and the ion detector 22. The mass spectrometry controller 23 includes an electrometer 24 that arithmetically produce the intensity of an ion detected by the ion detector 22. The main controller 13 includes an arithmetic operating unit 26 for performing a predetermined arithmetic operation or calculation based on the ion intensity calculated by the electrometer 24. The arithmetic operating unit 26 is configured of, for example, a combination of an operating and controlling device of a computer and software of a computer.

The casing 18 is additionally provided with a turbo molecular pump 27 and a rotary pump 28. The rotary pump 28 roughly reduces the pressure in the analysis chamber R1. Then, the turbo molecular pump 27 further reduces the pressure in the analysis chamber R1 which has been roughly reduced by the rotary pump 28 to vacuum or to a depressurized state close to vacuum. Pressure in the analysis chamber R1 is detected by an ion gauge 36, which is a pressure gauge. Then, the detection results of the ion gauge 36 are sent as an electric signal to the main controller 13.

Figure 2:
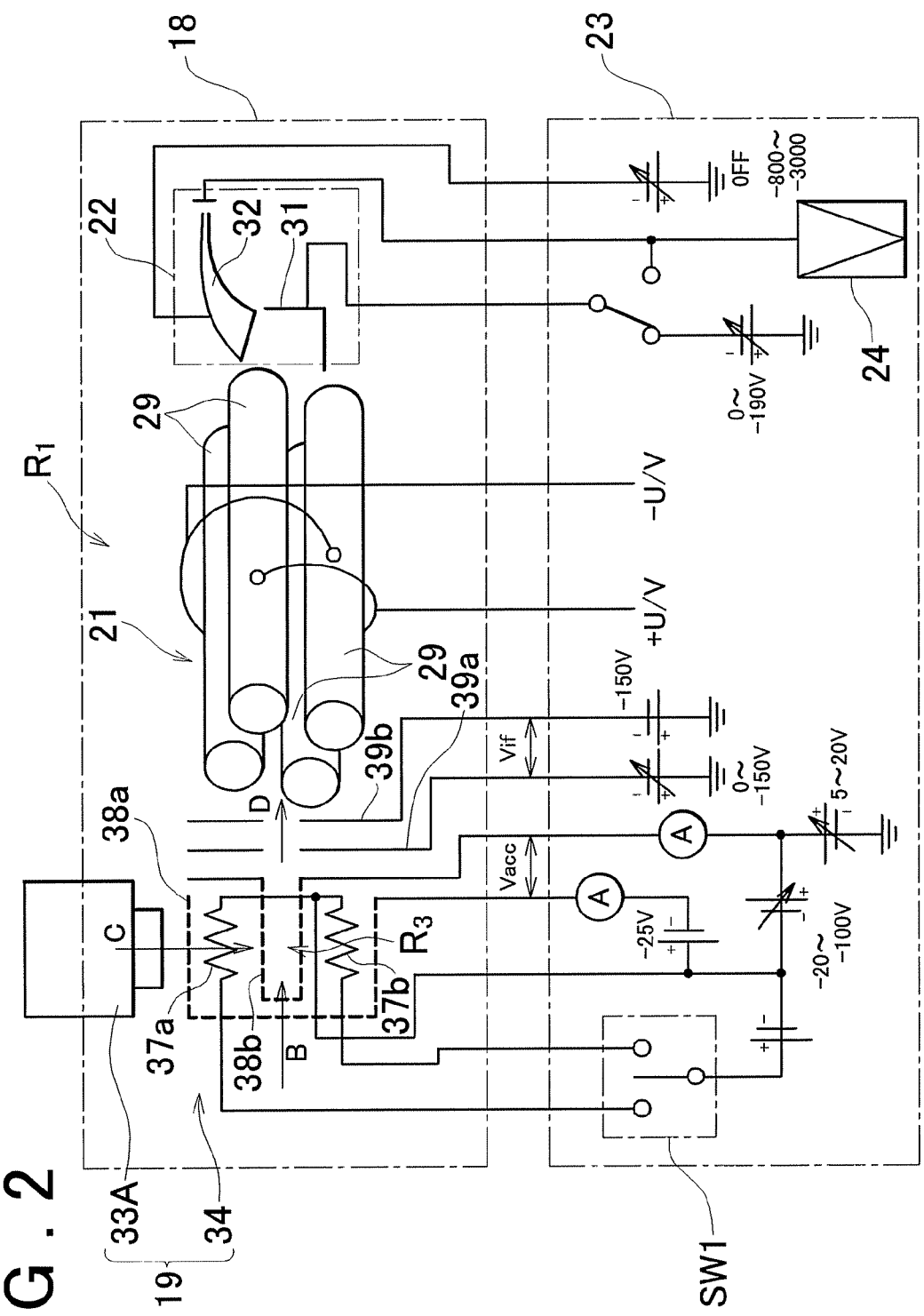
FIG. 2 is a view showing the configuration of the main part of FIG. 1 and the accompanying circuitry configuration.

The quadrupole filter 21 includes four electrodes 29 as illustrated in FIG. 2. A scanning voltage is applied to the electrodes 29. The scanning voltage is formed by superposing a high-frequency alternating voltage whose frequency changes with the passage of time and a predetermined magnitude of a direct-current voltage to each other. With this high-frequency scanning voltage being applied to the quadrupole electrodes 29, ions passing among these quadrupole electrodes 29 are separated for each mass-to-charge ratio of molecules, namely every mass-to-charge ratio. Then, each ion as thus separated is introduced into the ion detector 22 provided downstream, or behind.

The ion detector 22 includes an ion deflector 31 and an electron multiplier 32. The ions selected by the quadrupole filter 21 are collected to the electron multiplier 32 by means of the ion deflector 31, and then are output from the electron multiplier 32 as an electrical signal. The signal is counted by the electrometer 24 for being output as an ion intensity signal.

Now, the ionizer 19 shown in FIG. 1 includes a lamp 33A for PI (Photo-Ionization) and an EI (Electron Ionization) device 34. The lamp 33A functions as light emitting means. The lamp 33A for PI may be an L2D2 lamp (type: L7292), which is a discharge tube manufactured by Hamamatsu Photonics K.K. The specifications of this lamp are as follows:

Wavelength of radiation light: vacuum ultraviolet rays
  Gas for use: deuterium gas
  Starting voltage: 10±1 V
  Starting current: 0.8 A
  A rated voltage: 2.5 to 6.0 V
  A rated current: 0.3 to 0.6 A
  Distribution of Light intensity: FIG. 4(a)

Here, the lamp 33A of FIG. 4(a) is a lamp that emits divergent light having angularly spreading within approximately 10 degrees on one side, and thus 20 degrees on both sides. This lamp emits light with an angle range remarkably wider than that of laser light. When a deuterium gas is employed in the lamp, energy of light emitted therefrom is 10.2 eV.

The lamp 33A that has penetrated the casing 18 is fixed to the casing 18. The portion of the casing 18 to which the lamp 33A is fixed is sealed with a sealing member in an airtight manner. A light-emitting surface of the lamp 33A faces the EI device 34. The end portion of the lamp 33A which is opposite to the light-emitting surface thereof is positioned outside of the casing 18. In general, the lamp 33A (in particular, a lamp that emits vacuum ultraviolet light) extremely suffers life deterioration due to heat in vacuum and therefore is difficult to be used. However, if a part of the lamp 33A is placed in atmospheric air, as in the present embodiment, life deterioration thereof can be reduced to occur.

Figure 3:
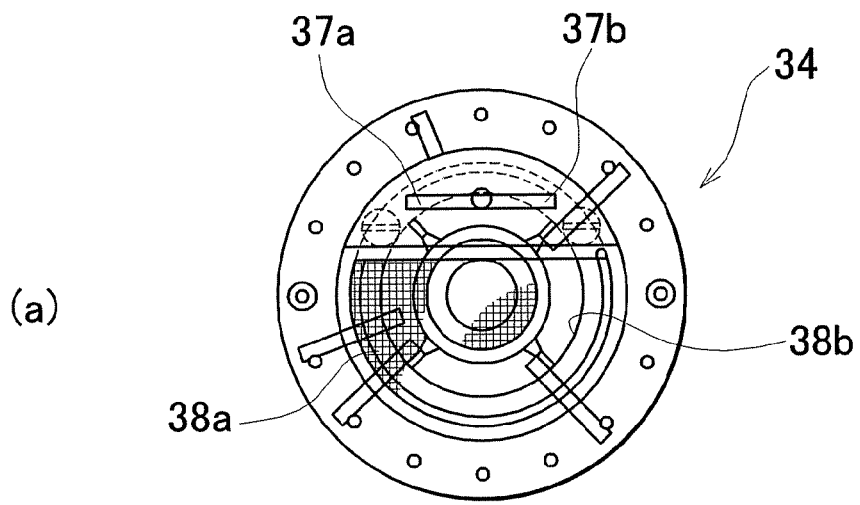
FIG. 3 is a view showing an appearance of an example of an ionizer, in which (a) is a top surface view and (b) is a side view.
Figure 3:
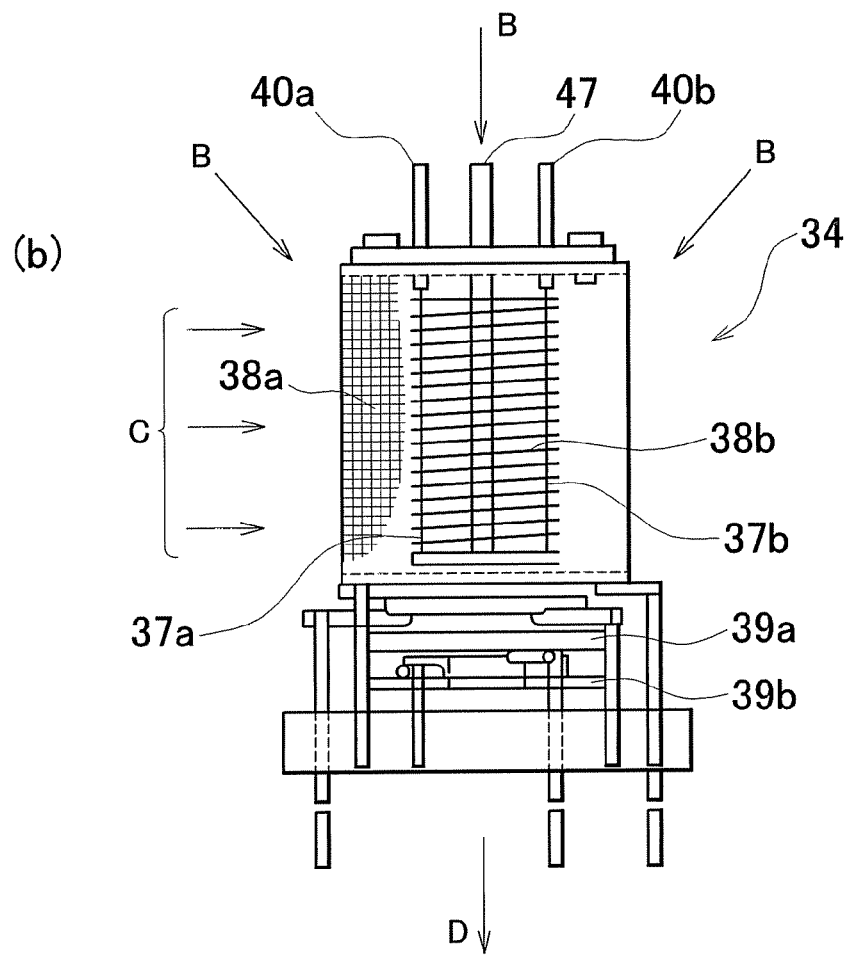

The EI device 34 has a plan configuration illustrated in (a) of FIG. 3 and a side elevation configuration depicted in (b) of FIG. 3. The EI device 34 includes a set of filaments 37a and 37b as electron generating means that emits electrons when an electric current is applied thereto, an external electrode 38a surrounding these filaments, and an internal electrode 38b paired with the external electrode 38a. The external electrode 38a and the internal electrode 38b both have a structure capable of transmitting light incident in a direction indicated by an arrow C. Specifically, the external electrode 38a is an electrode formed in a mesh shape, whilst the internal electrode 38b is an electrode in a spiral shape. Both these electrodes have a shape capable of light transmission.

The filament 37a and the filament 37b are both formed in a straight wire shape. These filaments are drawn out to the outside by electrodes 40a and 40b, respectively. A center electrode 47 is a common electrode for the filaments 37a and 37b. The filament 37a and the filament 37b are separate filaments, which are provided away from the common electrode 47 at a distance equivalent to each other. A gas to be measured (that is, a gas to be ionized) is introduced into the EI device 34 along a direction indicated by an arrow B, light emitted from the PI lamp 33a (refer to FIG. 1) is applied to the EI device 34 from directions indicated by arrows C, and then obtained ions are taken out to a direction indicated by an arrow D.

The internal structure of the EI device 34 is illustrated in a left portion of FIG. 2. The filaments 37a and 37b are provided in the electric field formed between the external electrode 38a and the internal electrode 38b. The inside of the internal electrode 38b is an ionizing region R3 where gas is ionized. When an electric current is applied to the filament 37a or 37b, electrons are generated from thus electrified filament.

A predetermined electron acceleration voltage Vacc is applied between the external electrode 38a and the internal electrode 38b. Now, assuming that the potential of the internal electrode 38b is V1 and the potential of the external electrode 38a is V2, Vacc is equal to "V2−V1" (that is, Vacc=V2−V1). If V2 is larger than V1 (V2>V1), Vacc is in a plus potential state (Vacc>0). If V2 is equal to V1 (V2=V1), Vacc is in a zero potential state (Vacc=0). If V2 is smaller than V1 (V2<V1), Vacc is in a minus potential state (Vacc<0).

When Vacc>0 (V2>V1), electrons which are present within and around the ionizing region R3 are accelerated in a direction away from the ionizing region R3. When Vacc<0 (V2<V1), electrons which are present around the ionizing region R3 are accelerated toward the ionizing region R3. When Vacc=0, electrons which are present within and around the ionizing region R3 are not accelerated.

On the other hand, the gas to be measured passes through the external electrode 38a, the filaments 37a and 37b, and the internal electrode 38b in the direction as shown by the arrow B, resulting in being supplied to the ionizing region R3. While the gas is being supplied into the ionizing region R3, when the accelerated electrons enter the ionizing region R3, these electrons collide with the gas, thereby ionizing the gas. Gas ionization performed in such a manner is called EI (electron ionization). With a predetermined voltage applied between lead-in electrodes 39a and 39b, the aforesaid generated ions are forcefully led to the quadrupole filter 21 positioned in the direction shown by the arrow D in the drawing.

Now, regarding the external electrode 38a and the internal electrode 38b, which are paired electrodes that generate the electron acceleration voltage Vacc in the present embodiment, the external electrode 38a is formed of a mesh-shaped electrode, whilst the internal electrode 38b is formed of a spiral-shaped electrode. Therefore, when the PI lamp 33A is turned on and emits light, the light is supplied through opening portions of the electrodes 38a and 38b to the ionizing region R3. When a gas is supplied in the direction shown by the arrow B into the ionizing region R3 while light from the PI lamp 33A is being supplied to the ionizing region R3, the gas is ionized with the light from the PI lamp 33A. This ionization is called PI (photo-ionization). With a predetermined voltage applied between the lead-in electrodes 39a and 39b, the aforesaid generated ions are also forcefully led to the quadrupole filter 21 positioned in the direction shown by the arrow D in the drawing.

In the present embodiment, the PI lamp light having a directivity lower than laser light and traveling in a spreading manner with a wavelength being in a vacuum ultraviolet range is used, and the light is applied to the ionizing region R3, which is a region immediately downstream of a gas outlet of the gas conveyor 4 of FIG. 1. Therefore, the entire gas exiting the gas outlet and traveling in a spreading manner at a high speed can be sufficiently ionized within a short time.

Now, the mass spectrometry controller 23 of FIG. 1 includes a circuitry configuration illustrated in FIG. 2. The mass spectrometry controller 23 will now be described with reference to this figure. The mass spectrometry controller 23 includes a switch SW1 for switching a set of the filaments 37a and 37b. Operation of the switch SW1 can select either one of the filaments 37a or 37b for allowing electric current to flow. In this technology, when either one of the filament 37 and the filament 37b cannot be lighted up due to some troubles, only by operating the switch SW1 the other normal filament may be selected to be lighted up to enable to continue generation of electrons. If such a compensation process is not required, only one filament may be employed.

The mass spectrometry controller 23 applies a potential V2 to the external electrode 38a and a potential V1 to the internal electrode 38b. As a result, an electron acceleration voltage Vacc is applied between the external electrode 38a and the internal electrode 38b. In the present embodiment, as described above, the electron acceleration voltage Vacc may be one of three types of electrical potentials, that is, Vacc>0 (plus potential state), Vacc=0 (zero potential state), and Vacc<0 (minus potential state).

The mass spectrometry controller 23 applies a lead-in voltage Vif between the pair of lead-in electrodes 39a and 39b. The lead-in voltage Vif includes at least two types of prepared voltage, one of which is a standard voltage, and the other of which is a voltage higher than the standard voltage. The higher voltage is a voltage causing a large drawing force for drawing ions. The standard voltage is a voltage suitable for EI, whilst the higher voltage is a voltage suitable for PI. The higher voltage for PI is set for the purpose of compensation because the amount of ionization in PI tends to be smaller than the amount of ionization in EI.

The mass spectrometry controller 23 applies the voltage (U/V) obtained by superposing a high-frequency voltage onto a direct-current voltage to each of the electrodes of the quadrupole filter 21. The aforesaid high-frequency voltage is a voltage with its frequency changing with the lapse of time. With this change of voltage in frequency, the ions can be separated according to the mass-to-charge ratio of one type, and be transferred to a latter stage.

Referring back to FIG. 1, the gas conveyor 4 connecting the sample chamber R0 and the analysis chamber R1 includes an inner tube 41 for conveying the gas, an outer tube 42 surrounding the inner tube 41, and a rotary pump 43 serving as exhaust means that exhausts air from an intermediate chamber R2 formed between the outer tube 42 and the inner tube 41. A mass flow meter 46 is provided as flow-rate adjusting means in front of the rotary pump 43. With the exhaust operation of the rotary pump 43, the inside of the intermediate chamber R2 can be set at a pressure lower than that of the sample chamber R0. The pressure inside the intermediate chamber R2 is detected by a crystal gauge 44, which is a pressure gauge. The detection results are sent as an electrical signal to the main controller 13.

The mass flow meter 46 is an element that allows gas to flow between an exhaust path of the rotary pump 43 and an external pressure (atmospheric pressure in the present embodiment). For example, when atmospheric gas is introduced into the exhaust path of the rotary pump 43 by the mass flow meter 46, the pressure of the intermediate chamber R2 kept by the rotary pump 43 can be increased. For example, the pressure initially kept at $10^2$ Pa can be increased to $10^3$ Pa.

By constructing the gas conveyor 4 as mentioned, the outside of the outer tube 42 (that is, the inside of the sample chamber R0) can be set at a high pressure, the intermediate chamber R2 can be set at an intermediate pressure, the inside of the inner tube 41 (that is, the inside of the analysis chamber R1) can be set at a low pressure, and these pressures can be kept constant. For example, the sample chamber R0 can be kept at an atmospheric pressure of about $10^5$ Pa, the inside of the intermediate chamber R2 can be kept at an intermediate pressure of about $10^2$ Pa, and the inside of the analysis chamber R1 can be kept in a vacuum state of about $10^{-3}$ Pa. The configuration in which exhaust operation forms an intermediate pressure between a high pressure and a low pressure as mentioned above may be referred to as a differential pumping structure.

The above differential pumping structure reliably achieves a function of conveying the gas generated in the sample chamber R0 via the inner tube 41 to the analysis chamber R1 while a pressure difference is maintained between the sample chamber R0 and the analysis chamber R1 inner pressures of which are different from each other. Here, in the present embodiment, an end of each of the inner tube 41 and the outer tube 42 on a sample chamber R0 side is formed as an orifice (that is, a micropore), and its facing end on an analysis chamber R1 side is formed as an opening with a normal size not achieving an orifice effect. The diameter of the orifice is, for example, about 100 μm. Forming orifice on the end of each of the inner tube 41 and the outer tube 42 on a sample chamber side, and forming a normal opening on the opposite end of those tubes on an analysis chamber side, as mentioned above, enable to efficiently collect gas generated from the sample S through the orifices and also efficiently convey it to the analysis chamber R1.

An operation of the gas analyzer 1 constructed as mentioned above will be described. In the present embodiment, turning on and off the PI lamp 33A, turning on and off current flow to the filament 37a or 37, and the value of the electron acceleration voltage Vacc applied to the electrodes 38a and 38b are controlled respectively. As a result, one measurement can be selectively performed from three types of measurements, that is, a measurement of the generated gas based on ionization only with PI, a measurement of the generated gas based on ionization only with EI, and a measurement of the generated gas based on PI+EI (that is, ionization with both of PI and EI). Now, these measurements will be described individually.

Measurement Based on Ionization Only Using EI

First, in FIG. 1, the sample S is fitted at the forward end of the sample tube 8, and then the sample tube 8 is inserted in the casing 6. Thus, the sample S is placed at a predetermined position in the sample chamber R0, that is, near an orifice portion of the gas conveyor 4. Subsequently, the rotary pump 28 and the turbo molecular pump 27 additionally provided to the analysis chamber R1 are activated to set the inside of the analysis chamber R1 in a vacuum state of about $10^{-3}$ Pa. Also, the rotary pump 43 additionally provided to the gas conveyor 4 is activated to set the pressure in the intermediate chamber R2 at an intermediate pressure of about $10^2$ Pa. Further, the inside of the sample chamber R0 is set at atmospheric pressure, for example, about $10^5$ Pa.

Next, in the ionizer 19,
(1) the lamp 33A for PI in FIG. 2 is put out to be set at "OFF" where it does not emit light,
(2) the filament 37a or 37b is supplied with current to be set at "ON" where it emits electrons, and
(3) the electron acceleration voltage Vacc to be applied to the electrodes 38a and 38b is set as Vacc<0 (namely, V2<V1).

With the setting of Vacc<0 (V2<V1), electrons generated from the filament 37a or 37b are accelerated toward the ionizing region R3. The accelerated electrons collide with the gas in the ionizing region R3 to ionize the gas. In other words, making conditions listed above as (1) to (3) realizes ionization using only EI.

After completion of making the aforesaid condition, the temperature controller 12 shown in FIG. 1 controls the heating furnace 7 to generate heat according to a predetermined program, to thereby increase the temperature of the sample S according to the predetermined program. The conditions for increasing temperature are varied according to a sample and a method of measurement. For example, the temperature is increased for a certain period of time selected from approximately thirty minutes to two hours with a certain temperature gradient selected from 2 degrees Celsius/minute to 10 degrees Celsius/minutes. While the temperature increasing, when a gas is departed from the sample S according to the characteristics of the sample S, the gas is drawn by the outer tube 42 and the inner tube 41 through each orifice portion thereof to flow into the inside of the inner tube 41. The gas is subsequently supplied to the ionizer 19 through the opening of the inner tube 41.

The gas supplied to the ionizer 19 enters the inside of the ionizing region R3 in FIG. 2, and is ionized through collision of electrons generated from the filament 37a or 37b and accelerated with the electron acceleration voltage Vacc. This ionization is called EI (electron ionization). This ionization process is successively performed during the measuring operation. In the EI, ions from the gas components are fragmented by collision against the electrons response to a degree of collision and, as a result, fragment ions (that is, fragment components or broken pieces) are generated.

Ions from which fragment ions are derived are called parent ions. The ratio of occurrence of fragment ions with respect to parent ions is changed according to the energy amount of the electrons. Specifically, if the amount of electron energy is small, the amount of parent ions becomes large, whilst the amount of fragment ions becomes small. On the other hand, if the amount of electron energy is large, the amount of fragment ions becomes large, whilst the amount of parent ions becomes small. If the amount of electron energy is extremely large, most of the ions may become fragment ions and there may be almost no parent ions.

The parent ions and fragment ions both generated in the above-described manner are led by the lead-in voltage Vif to be conveyed to the quadrupole filter 21. A high-frequency voltage whose frequency is changed with the lapse of time is applied to the quadrupole electrodes 29 in the quadrupole filter 21. Therefore, only the ions having a mass-to-charge ratio corresponding to each frequency are selected to go forward to the ion detector 22. That is, the ions separated according to the mass-to-charge ratio are sent to the ion detector 22 on a time-series basis according to the mass-to-charge ratio.

In the ion detector 22, the ion deflector 31 collects the ions and sent them into the electron multiplying tube 32. The electron multiplier 32 multiplies ions under a predetermined process and then output them as an electric signal. Subsequently, the electrometer 24 calculates ion intensity for each mass-to-charge ratio based on the output signal. The range in which the frequency of the high-frequency voltage may change and a step width by which frequency changes are both determined in accordance with mass-to-charge ratios desired for measurement. For example, if the ions are desired to be separated within a range of mass-to-charge ratios of m/e=10 to 200 by scanning the frequency of the high-frequency voltage applied to the quadrupole filter 21, the desired range of mass numbers can be scanned by changing frequency for a scanning time of about five seconds. In the present embodiment, scanning of frequencies is successively repeated by cycles during the measuring operation.

As can be understood from the foregoing, in the present embodiment, when a gas is generated from the sample S at a certain instant in the sample chamber R0 of FIG. 1, the gas is not trapped by gas trap means, such as a gas chromatograph, but is conveyed directly and simultaneously to the ionizer 19 for simultaneous ionization. Then, the ions are separated by the quadrupole filter 21 according to the mass-to-charge ratio, that is, for each component ion and each ion fragmented from the component ion, and the ion intensity is found for the separated individual component ions and the like.

That is, in the present embodiment, when a gas containing several gas components is generated at a certain instant, each gas component is subjected to an ion-intensity measurement process in real-time at the time of generation of the gas. Here, real-time means that the gas is supplied to a mass spectrometer unit at the instant when the gas is generated and also a plurality of gas components contained in the generated gas are successively and approximately simultaneously subjected to mass spectrometry within an extremely short period of time.

Thus, the ion intensity of the gas which has been ionized with the EI is obtained for each mass-to-charge ratio. Obtained results are then stored in a predetermined region in a memory (that is, a storage medium) in the main controller 13. The main controller 13 reads the stored ion intensity data regarding the sample S from the memory at a desired point of time for printing it by the printer 14 or for displaying it on the screen of the display 16 as an image.

Figure 5:
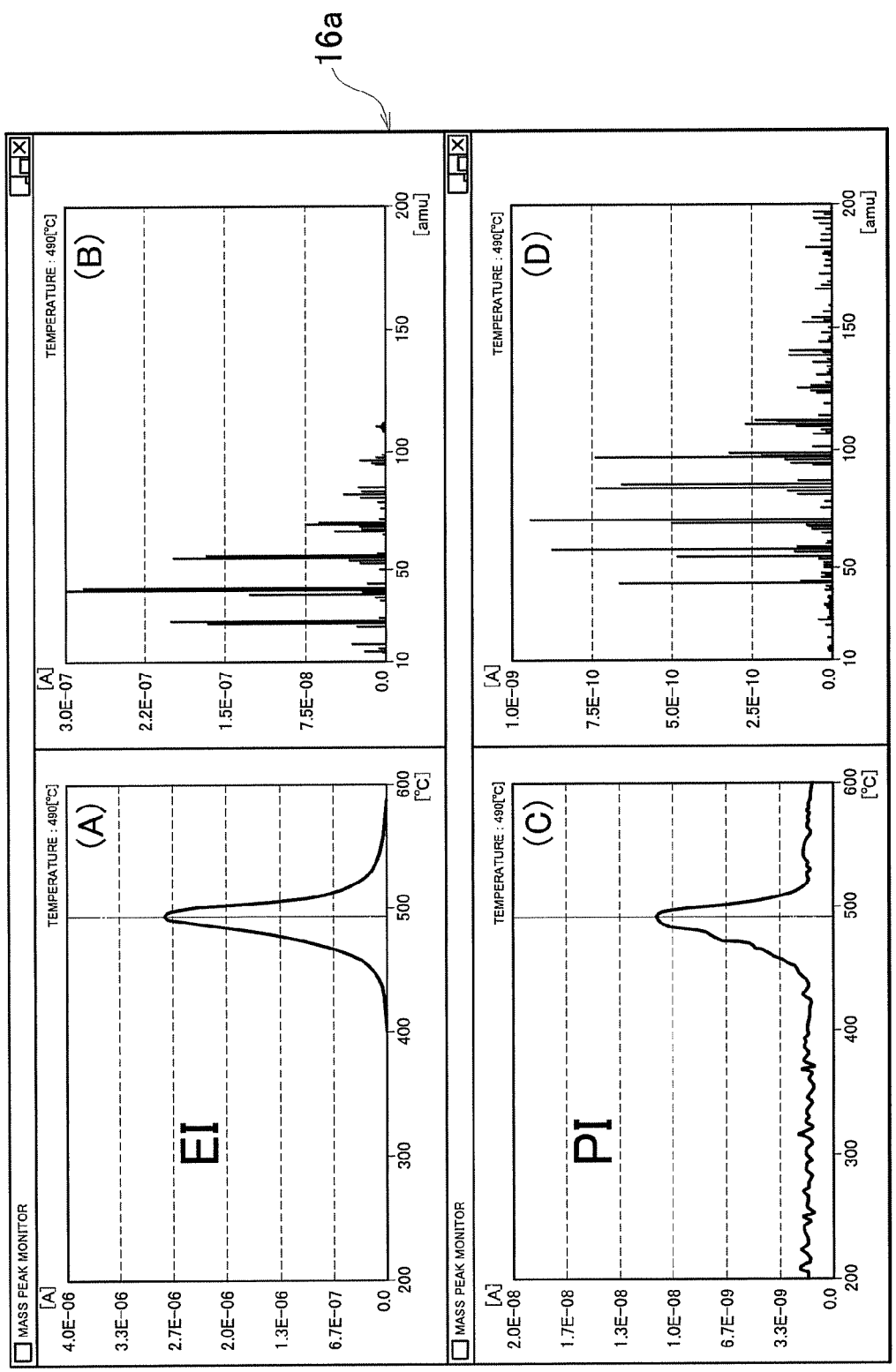
FIG. 5 is a view showing an example of image displays of measurement results obtained by using the gas analyzer according to the present invention.

FIG. 5 illustrates images of graphs displayed on a screen 16a of the display 16 of FIG. 1 for depicting one example of measurement results. This display example depicts measurement results when a low-density polyethylene is taken as a sample. Two images (A) and (B) displayed on an upper portion in the screen 16a depict the measurement results obtained when the gas is ionized only with the EI. Also, two images (C) and (D) displayed on a lower portion in the screen 16a depict the measurement results obtained when the gas is ionized only with the PI (namely, photo-ionization) to be described later. FIG. 5 illustrates both the measurement results based on the EI method and the measurement results based on the PI method simultaneously on one screen. Alternatively, the measurement results (A, B) based on the EI method and the measurement results (C, D) based on the PI method may be displayed separately.

In each of the EI measurement results (A, B) and the PI measurement results (C, D) in FIG. 5, the graphs (A, C) on the left side are total ion-intensity charts which depict whole changes in ion intensity of gas generated every moment during increasing of temperature. In these graphs, the lateral axis represents sample temperature, whilst the longitudinal axis represents ion intensity. Gas which is generated from the sample at a certain sample temperature contains the component ions or their fragment ions. The graphs (B, D) on the right side of the screen 16a are graphs which depict mass spectrums of the ion intensity of the above component ions or their fragment ions, for each mass-to-charge ratio. In these graphs, the lateral axis represents the mass-to-charge ratio, whilst the longitudinal axis represents ion intensity.

In mass spectrometry (A, B) based on the EI method, as depicted in the graph of the total ion-intensity chart (A), a gas is generated from the sample at a temperature of 490° C. (degree Celsius). The plurality of gas components contained in the generated gas each has a peak at the mass-to-charge ratio inherent in the sample, as depicted in the graph (B) of mass spectrum. As described above, when ionization is performed based on the EI method, fragment ions are generated. Therefore, the mass spectrum includes peaks of fragment ions other than peaks of the parent ions. The mass spectrum graph (B) cannot teach which peaks of the parent ions are and which the fragment ions are. Also, the ratio of occurrence of peaks of the fragment ions against peaks of the parent ions is varied depending on the magnitude of the energy amount of the electrons to be colliding with the gas.

Measurement Based on Ionization Only Using PI

Now, a measurement based on the PI method will be described. First, as in the same manner as the measurement based on the EI method, the sample S is fitted at the forward end of the sample tube 8 of FIG. 1, and then the sample tube 8 is inserted in the casing 6. Thus, the sample S is placed at a predetermined position in the sample chamber R0. Next, the pressures within the analysis chamber R1, the intermediate chamber R2 of the gas conveyor 4, and the sample chamber R0 are respectively set in a manner similar to that of a measurement based on the EI method.

Now, regarding the ionizer 19,
(1) the PI lamp 33A in FIG. 2 is put on to be set at "ON" where it emits vacuum ultraviolet light spreading within a wide angle range,
(2) the filament 37a or 37b is not supplied with current to be set at "OFF" where it does not emit electrons, and
(3) the electron acceleration voltage Vacc to be applied to the electrodes 38a and 38b is set as Vacc=0 (namely, V2=V1) or Vacc>0 (namely, V2>V1).

After completion of making the aforesaid condition, the temperature controller 12 shown in FIG. 1 controls the heating furnace 7 to generate heat according to a predetermined program, to thereby increase the temperature of the sample S according to the predetermined program. While the temperature increasing, when a gas is departed from the sample S according to the characteristics of the sample S, the gas is drawn by the outer tube 42 and the inner tube 41 through each orifice portion thereof to flow into the inside of the inner tube 41. The gas is subsequently supplied to the ionizer 19 through the opening of the inner tube 41.

The gas supplied to the ionizer 19 enters the inside of the ionizing region R3 in FIG. 2, and is ionized with light (vacuum ultraviolet light in the present embodiment) emitted from the PI lamp 33A based on the PI method. This ionization process is also successively performed during the measuring operation. When the gas in the ionizing region R3 is irradiated with vacuum ultraviolet light to be ionized, the vacuum ultraviolet light also strikes the external electrode 38a, the internal electrode 38b, and the filaments 37a and 37b which are structures serving as secondary electron generating means, to thereby produce secondary electrons from these structures. If these secondary electrons enter the inside of the ionizing region R3, in addition to gas ionization with vacuum ultraviolet light, ionization due to collision of the secondary electrons with the gas occurs. That is, EI occurs. In such a condition, a measurement employing ionization based on only PI method cannot be accurately performed.

If the secondary electrons enter the inside of the ionizing region R3, they can provide the sample molecules with an electronic impact. PI is essentially a suitable method for generating molecular ions (namely, parent ions) of sample molecules that are ionized with occurring of fragment ions by EI because ionizing energy of EI is too high. However, in the present embodiment, secondary electrons as described above can cause EI to thereby change part of sample molecules into fragment ions. According to the present embodiment, however, the external electrode 38a that can collect the electrons (that is, secondary electrons) generated due to irradiation of ultraviolet light in the ionizing region R3 is provided in a region outside of the ionizing region R3. Therefore, entrance of the secondary electrons into the ionizing region R3 can be suppressed, thereby reducing the generation of fragment ions during an operation of PI.

Specifically, in the present embodiment, as in the above condition (3), the electron acceleration voltage Vacc is set as Vacc=0 (namely, V2=V1) or Vacc<0 (namely, V2>V1). Therefore, even if secondary electrons are generated from the structures, these secondary electrons are accelerated in a direction away from the ionizing region R3 to be prevented from entering the inside of the ionizing region R3. Thus, no ionization due to an electronic impact occurs in the ionizing region R3. As a result, ionization is performed only by vacuum ultraviolet light from the lamp 33A. In this ionization carried out by using PI, fragment ions are rarely generated, and only parent ions are generated.

The ions of the gas which is ionized only by the PI method as described above are separated for each mass-to-charge ratio by the quadrupole filter 21, in the same manner as a measurement based on the EI method. Thereafter, the ion intensity is obtained by the ion detector 22 and the electrometer 24. As descried above, also in a measurement based on the PI method, when a gas is generated from the sample S at a certain instant in the sample chamber R0 of FIG. 1, the gas is not trapped by gas trap means, such as a gas chromatograph, but is conveyed directly and simultaneously to the ionizer 19 for simultaneous ionization. Then, the ions are separated for each mass-to-charge ratio, and hence for each component ion, by the quadrupole filter 21. Then, the ion intensity is obtained for the separated individual component ions. In other words, upon gas occurrence, mass spectrometry is performed on each gas component in real-time.

Thus, the ion intensity of the gas which is ionized by using the PI is obtained for each mass-to-charge ratio, and the results obtained are stored in a predetermined region in the memory in the main controller 13. The main controller 13 reads thus stored ion intensity data for the sample S from the memory at a desired point of time for printing by using the printer 14 or for displaying on the screen of the display 16 as an image.

For example, representations as depicted in the graph (C) of the total ion-intensity chart on the lower portion of FIG. 5 and the graph (D) of the mass spectrum similarly on the lower portion thereof are displayed as measurement results based on the PI method. In mass spectrometry based on the PI method, as depicted in the graph (C) of the total ion-intensity chart, a gas is generated from the sample at a temperature of 490° C. (degrees Celsius). The plurality of component ions contained in the generated gas each have a peak at a mass-to-charge ratio inherent in the sample as depicted in the graph (D) of the mass spectrum.

When ionization is performed based on the PI method, generation of fragment ions as observed in the case of ionization based on the EI method is significantly suppressed. Therefore, all peaks depicted in the graph (D) of mass spectrum are derived from parent ions, and no fragment ions are contained at all. Though the mass spectrum (B) based on the EI method does not give the components of the generated gas, the components of the generated gas is easily given in view of the mass-to-charge ratio in the mass spectrums (D) based on the PI method. On the other hand, the mass spectrum (B) based on the EI method enables to realize an analysis which is based on information of fragment ions, and in which no decision can be made only by information of parent ions.

In the device according to the present embodiment, when ionization based on the PI method is performed, the PI lamp 33A emits a light that travels while angularly spreading, rather than a highly directive light, such as laser light. Thus, the opening of the gas conveyor 4 is widely covered with the light emitted. In general, gas has a property of spreading and scattering within a short period of time, and therefore a highly directive light, such as laser light, can locally ionize the gas, but it is difficult for such a highly directive light to sufficiently ionize the whole gas discharged within a short period of time. On the contrary, in the present embodiment, a low directive light which spreads and scatters, in particular, vacuum ultraviolet light, is applied to the front of the gas outlet, so that the gas discharged within a short period of time can be sufficiently ionized. As a result, the plural molecular components contained in the gas are simultaneously ionized, so that the plurality of molecular components can be analyzed in real-time.

Here, when ionization is performed based on the PI method, the amount of ionized gas tends to be smaller than that in the case of ionization based on the EI method. Therefore, the accuracy of ion intensity analysis using the quadrupole filter 21 and the ion detector 22 in FIG. 1 may be worse compared with the case of the EI method unless any measure is taken. To solve this problem, when an analysis is performed based on the PI method in the present embodiment, the pressure in the intermediate chamber R2 of the gas conveyor 4 is desirably adjusted as follows.

Specifically, the inside of the sample chamber R0 has initially been set at atmospheric pressure (for example, $10^5$ Pa), the inside of the analysis chamber R1 has initially been set at a vacuum state (for example, $10^{-3}$ Pa), and the inside of the intermediate chamber R2 in the gas conveyor 4 has initially been set at an intermediate pressure (for example, $10^2$ Pa), respectively. Thereafter, the mass flow meter 46 is operated to leak (and hence exhaust) the gas, thereby increasing the intermediate pressure from $10^2$ Pa to, for example, $10^3$ Pa. With such an operation, the amount of gas entering from the sample chamber R0 to the analysis chamber R1 can be increased, thereby obtaining a sufficient amount of ions for measurement.

Measurement Based on PI+EI Ionization

Now, a measurement based on both ionizations of PI and EI will be described. First, as in the same manner as the measurement based on the EI method and the PI method, respectively, the sample S is fitted at the forward end of the sample tube 8 of FIG. 1, and then the sample tube 8 is inserted in the casing 6. Thus, the sample S is placed at a predetermined position in the sample chamber R0. Next, the pressures within the analysis chamber R1, the intermediate chamber R2 of the gas conveyor 4, and the sample chamber R0 are respectively set in a manner similar to that of a measurement based on the EI method.

Now, regarding the ionizer 19,
(1) the PI lamp 33A in FIG. 2 is put on to be set at "ON" where it emits vacuum ultraviolet light spreading within a wide angle range,
(2) the filament 37a or 37b is not supplied with current to be set at "OFF" where it does not emit electrons, and
(3) the electron acceleration voltage Vacc to be applied to the electrodes 38a and 38b is set as Vacc<0 (namely, V2<V1).

In the present embodiment, the vacuum ultraviolet light from the lamp 33A strikes the gas molecules in the ionizing region R3, to thereby perform PI. On the other hand, since no electrons are generated from the filaments 37a and 37b, EI does not seem to occur. However, the vacuum ultraviolet light from the lamp 33A strikes the structures, such as the filaments 37a and 37b, to thereby generate secondary electrons. Then, these secondary electrons are accelerated toward the ionizing region R3 by the electron acceleration voltage Vacc set as Vacc<0, resulting in causing EI by the secondary electrons thus accelerated. In other words, even when no electrons is generated by the filaments 37a and 37b which are components of the EI device 34 because they are not electrically energized, the EI is inevitably performed by turning on the PI lamp 33A to emit light and setting the electron acceleration voltage Vacc on Vacc<0. Consequently, ionizations based on both of PI and EI are performed in the ionizing region R3.

Note that, instead of the above condition (2), The filament 37a or 37b may be supplied with current to be set at "ON" where it emits electrons. In such a case, in addition to the secondary electrons generated from the filament 37a or 37b due to light, thermoelectrons are discharged from the filaments themselves, thereby increasing the amount of electrons to be supplied to the ionizing region R3.

After completion of making the aforesaid condition, in the same manner as measurements based on the PI method and the EI method, respectively, the temperature controller 12 shown in FIG. 1 controls the heating furnace 7 to generate heat according to a predetermined program, to thereby increase the temperature of the sample S according to the predetermined program. While the temperature increasing, when a gas is departed from the sample S according to the characteristics of the sample S, the gas is drawn by the outer tube 42 and the inner tube 41 through each orifice portion thereof to flow into the inside of the inner tube 41. The gas is subsequently supplied to the ionizer 19 through the opening of the inner tube 41.

The gas supplied to the ionizer 19 enters the inside of the ionizing region R3 in FIG. 2, and is ionized with light emitted from the PI lamp 33A based on the PI method. Furthermore, the gas is also ionized by the secondary electrons generated from the structures based on the EI method. That is, ionization is performed based on both of the PI method and the EI method. As in the same manner as the measurement based on only the EI method and the measurement based on only the PI method, the ionized gas is separated by the quadrupole filter 21 for each mass-to-charge ratio, and then the ion intensity is obtained by the ion detector 22 and the electrometer 24.

Thus, the ion intensity of the gas ionized with both of PI and EI is detected for each mass-to-charge ratio, and the detection results are stored in a predetermined region in a memory in the main controller 13. The main controller 13 reads thus stored ion intensity data for the sample S from the memory at a desired point of time for printing by using the printer 14 or for displaying on the screen of the display 16 as an image.

Measurement results based on both of PI and EI are not displayed in FIG. 5. If a method of simultaneously performing PI and EI is used, analysis information based on PI and analysis information based on EI can be obtained from one sample at just the same time, and such information can be displayed on the screen. Since such information include both of parent-ion information and fragment-ion information, a highly accurate analysis can be performed on the sample.

Operation for Taking Difference

A measurement based on only EI, a measurement based on only PI, and a measurement based on PI+EI have been separately described above. In actual analysis, an analysis in which these three pieces of information are observed with being compared with each other is preferable in performing a highly reliable analysis. However, performing three types of measurement separately to obtain these three pieces of information is a loss in time, and the obtained results may have an error due to an error among these measurements. In the present embodiment, these problems are mitigated by an arithmetical operation in the main controller 13 of FIG. 1.

Specifically, the main controller 13 includes a program for causing the arithmetic operating unit 26 to subtract the measurement results based on only PI from the measurement results based on PI+EI in an arithmetic operation. That is, the arithmetic operating unit 26 takes a difference between the measurement results based on PI+EI and the measurement results based on only PI. After completion of two types of measurements, that is, a measurement based on PI+EI and a measurement based on only PI, the arithmetic operating unit 26 calculates the above operation for taking a difference, thereby obtaining the measurement results based on only EI without actually performing a measurement based on EI. This significantly saves time compared with the case of performing three types of measurement. Also, when an analysis is performed based on a plurality of measurement results, it is possible to mitigate a deterioration of analysis accuracy due to an error among a plurality of measurements.

It has been explained that a measurement based on only EI is omitted and information thereof is obtained through an arithmetic operation. Instead, measurement data based on only PI may be obtained through the arithmetic operation for taking a difference, after completion of two types of measurements, that is, a measurement based on PI+EI and a measurement based on only EI.

Furthermore, in the case where the measurement data based on only EI are calculated through the arithmetic operation, after completion of two types of measurement, that is a measurement based on PI+EI and a measurement based on only PI, no measurement based on EI is actually performed, so that a device for performing a measurement based on EI is not required. Therefore, in this case, the filaments 37$a$ and 37$b$ and the circuitry configuration for driving them, which are components of the EI device 34 in FIG. 2, are not required.

Note that it is impossible to dispense with the electrodes 38$a$ and 38$b$, which are also components of the EI device 34. The reason for this is that, firstly, these components are required to function as structures that generate secondary electrons with light discharged from the PI lamp 33A. Secondary, the electron acceleration voltage Vacc has to be generated by these structures in order to cause EI.

Timing for Measurement Based on Each Ionization Method

In the above description, it is assumed that three types of measurement are separately performed, that is, a measurement based on only EI, a measurement based on only PI, and a measurement based on PI+EI are separately performed. Specifically, it is assumed that the main controller 13 of FIG. 1 realizes an electron ionization mode (EI mode), a photo ionization mode (PI mode), and a photo-electron ionization mode (EI+PI mode), separately. In such a case, a first sample is subjected to a measurement based on one ionization method with a temperature-increasing program being applied to the same sample, a second sample is subjected to a measurement based on another ionization method with the temperature-increasing program being applied to the same sample separately from the first sample, and a third sample is subjected to a measurement based on still another ionization method with the temperature-increasing program being applied to the same sample separately from the first and second samples.

Instead of such a measurement mode, the following measurement mode can be adopted. Specifically, one sample S is disposed at a predetermined position in the sample chamber R0 in FIG. 1, and the temperature of the sample S is increased according to a predetermined temperature-increasing program. Simultaneously with this temperature increase, the ionizer 19 performs an ionization process. In this ionization process, the EI mode, the PI mode, and the PI+EI mode are successively repeated one by one at a predetermined time interval during the start to end of measurement. In this case, a time assigned for the process of each ionization mode is set to be equal to a time required for high frequency scanning a predetermined range of the mass-to-charge ratio by using the quadrupole filter 21 and further obtaining the ion intensity by using the ion detector 22. For example, if a process of separating ions by high-frequency wavelength scanning corresponding to the measurement range of the mass-to-charge ratio and a measurement of ion intensity for the separated ions require approximately five seconds, a time interval for each ionization process performed by the ionizer 19 in each ionization mode is also set at approximately five seconds.

Second Embodiment of the Gas Analyzer

Figure 6:
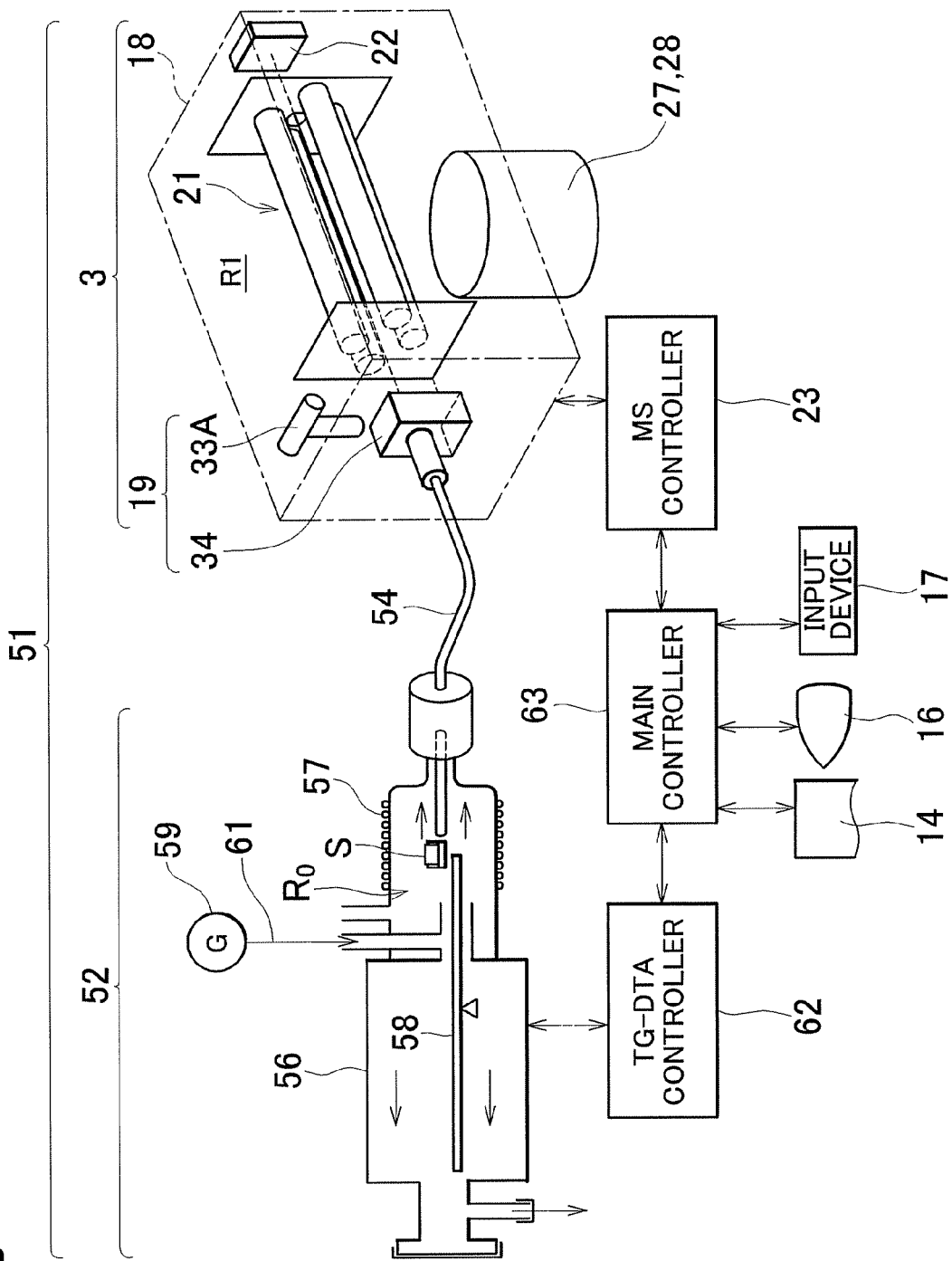
FIG. 6 is a partial perspective view showing another embodiment of the gas analyzer according to the present invention.

FIG. 6 shows another embodiment of the gas analyzer according to the present invention. A gas analyzer 51 illustrated therein includes a TG-DTA device 52 serving as a gas generator, an analyzer 3 that performs an analysis for a gas, and a capillary tube (that is, a tubule or a tube having a narrow inside diameter) 54 serving as gas conveying means provided between these devices for conveying a gas. The analyzer 3 is the same analyzer which is depicted by the same reference numeral in the embodiment shown in FIG. 1. Therefore, description of the analyzer 3 will be eliminated.

The TG-DTA device 52 is a device that performs both a TG (Thermogravimetry) measurement and a DTA (Differential Thermal Analysis) measurement at the same time. The TG-DTA device 52 includes a casing 56 that forms a sample chamber R0, a heating furnace 57 serving as heating means provided around the casing 56, and a balance beam 58 provided inside of the casing 56. A gas supply source 59 is connected via a piping 61 to the casing 56. The gas supply source 59 discharges a carrier gas, for example, an inert gas, for example, a helium (He) gas.

The heating furnace 57 is configured of a heater having a heating wire that is electrically energized and generates heat. The heating wire is a heating source for the heater. The heating furnace 57 generates heat according to an instruction from a TG-DTA controller 62 and further being cooled as required. The TG-DTA controller 62 is configured of a computer, a sequencer, a dedicated circuit, and the like. The TG-DTA controller 62 is activated based on an instruction from a main controller 63. The main controller 63 is configured to include a computer, for example.

In this TG-DTA device 52, the sample S is heated by the heating furnace 57 according to a predetermined temperature-increasing program to increase its temperature. When the sample S is thermally changed (for example, dissolved, decomposed, etc.) in response to its characteristics during the temperature of the sample rises, a change in weight occurs in the sample S, and a gas is also generated from the sample S. The TG-DTA device 62 measures the change in weight of the sample S via the balance beam 58. Also, a change in temperature of the sample S with respect to a reference material (not shown) disposed adjacently to the sample S is measured by a temperature sensor (for example, a thermocouple).

When a gas is generated from the sample S, the gas is conveyed via the capillary tube 54 to the ionizer 19 of the analyzer 3. The processes of the elements in the analyzer 3, that is, the ionizer 19, the quadrupole filter 21, and the ion detector 22, are the same as those in the embodiment in FIG. 1, and therefore their description is omitted herein. The capillary tube 54 is a simple tubule without a double tube structure as the gas conveyor 4 in FIG. 1 or a differential pumping structure. This capillary tube 54 keeps a vacuum in the analysis chamber R1 and an atmospheric pressure in the sample chamber R0 by the length and inner diameter of the tubule.

Also in the gas analyzer according to the present embodiment, when ionization based on the PI method is performed, not light with high directivity, such as laser light, but light that travels as angularly spreading is discharged from the PI lamp 33A to widely cover the opening of the capillary tube 54 for gas exhaust. In general, gas has a property of spreading and scattering within a short period of time, and therefore a highly directive light, such as laser light, can locally ionize the gas, but it is difficult for such a highly directive light to sufficiently ionize the whole gas discharged within a short period of time. On the contrary, in the present embodiment, a low directive light which spreads and scatters, in particular, vacuum ultraviolet light, is applied to the front of the gas outlet, so that the gas discharged within a short period of time can be sufficiently ionized. As a result, the plural molecular components contained in the gas are simultaneously ionized, so that the plurality of molecular components can be analyzed in real-time.

Third Embodiment of the Gas Analyzer

Figure 7:
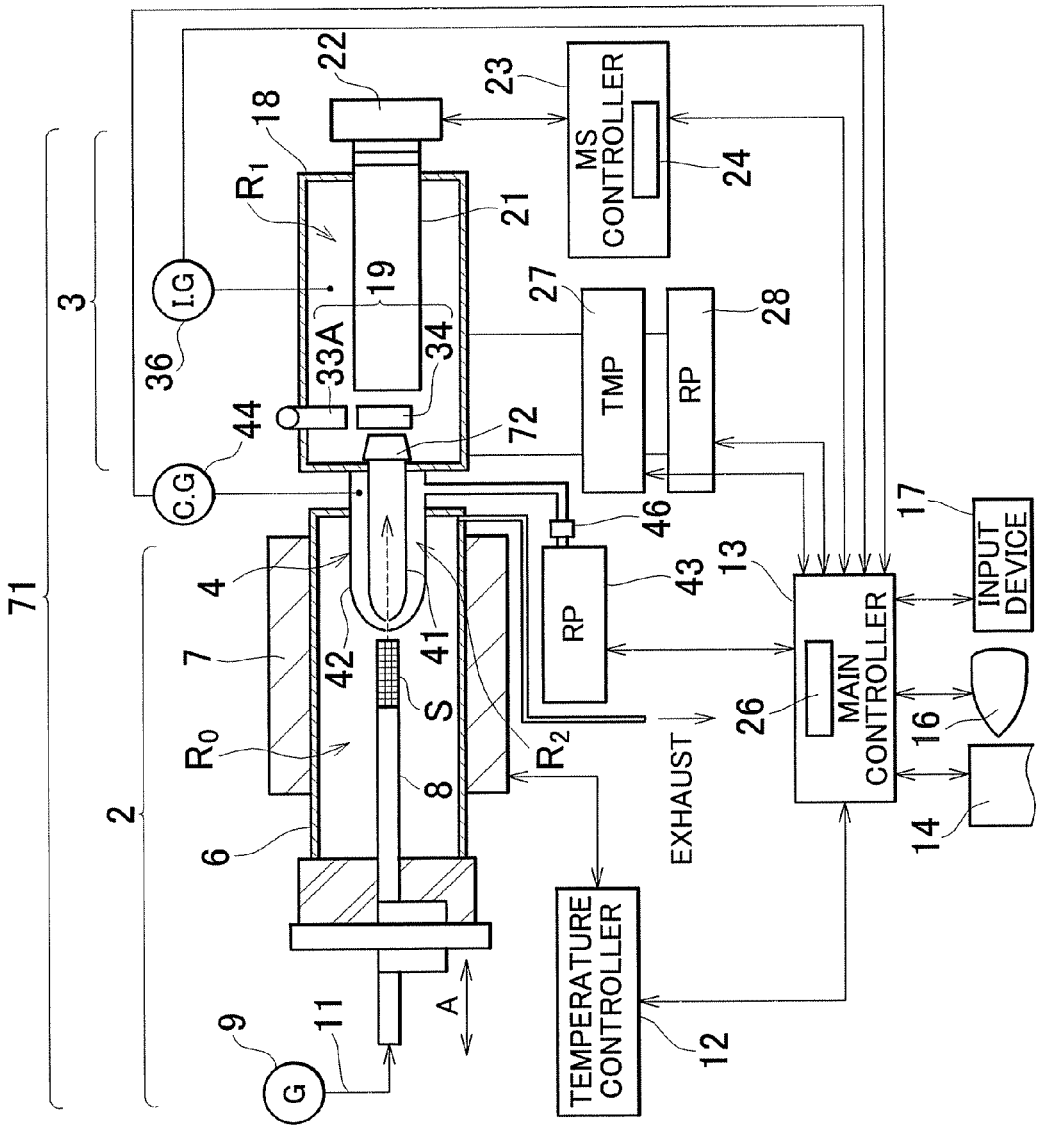
FIG. 7 is a partial perspective view showing still another embodiment of the gas analyzer according to the present invention.

FIG. 7 shows still another embodiment of the gas analyzer according to the present invention. A gas analyzer 71 depicted therein is the one obtained by modifying the above-described embodiment shown in FIG. 1. The gas analyzer 71 is different from the gas analyzer 1 shown in FIG. 1 in that a throttle member 72 is provided at a gas exhaust opening of the inner tube 41 of the gas conveyor 4. The other structures are the same as those in the embodiment of FIG. 1, and their description of the configuration will be omitted.

The throttle member 72 has a cone cylindrical shape (with a top being chipped or truncated) with an end face on an ionizer 19 side having a small diameter and an end face on a gas conveyor 4 side having a large diameter. The throttle member 72 narrows down a cross-sectional area of a gas flow flowing from the gas conveyor 4 to the ionizer 19, in a direction toward an analysis chamber R1 side from a sample chamber R0 side. Due to throttle function, a high-density gas can be sent into the ionizing region R3 of FIG. 2 and, as a result, the amount of gas to be ionized can be increased.

Modification Examples of the Ionizer

Figure 8:
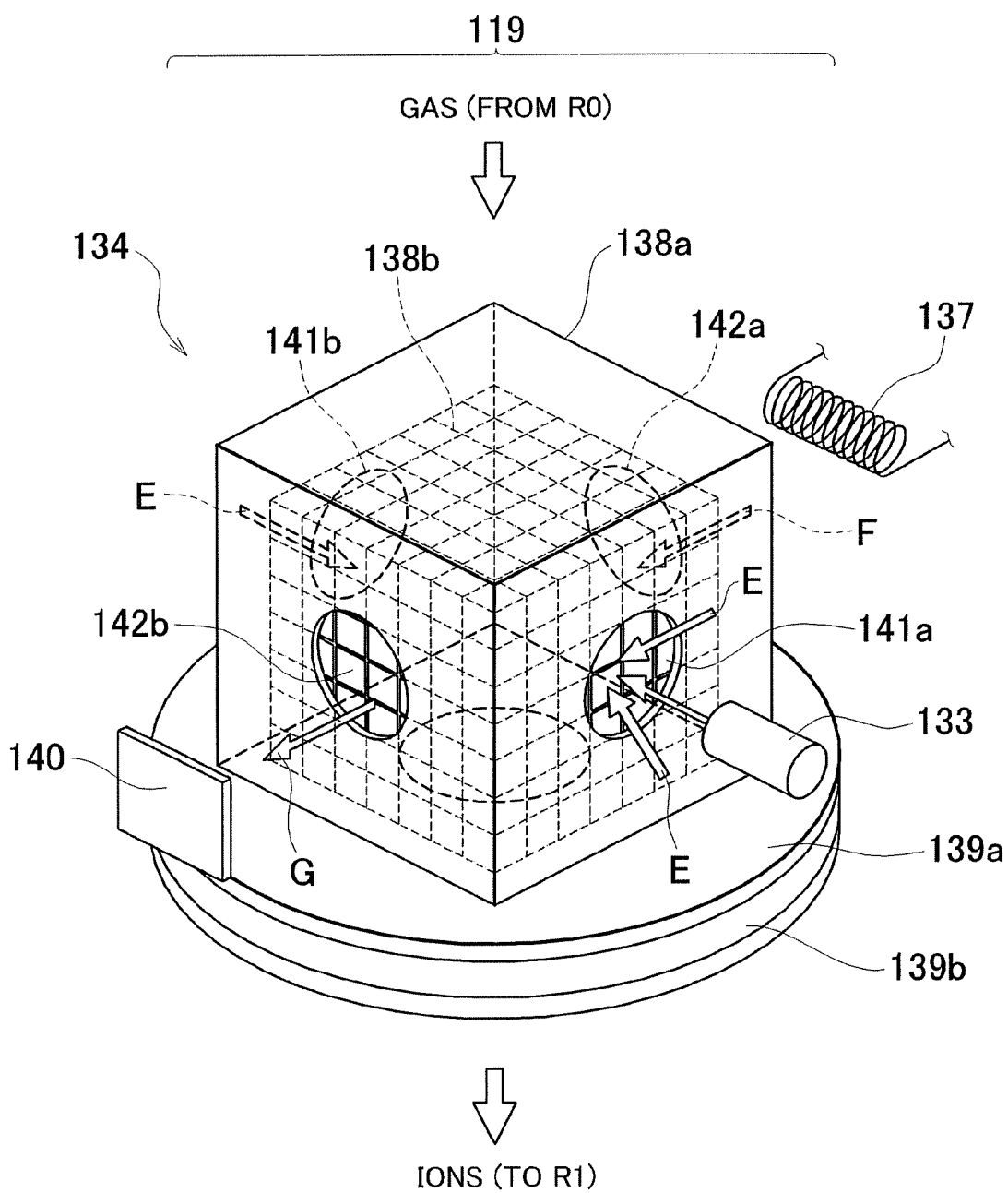
FIG. 8 is a perspective view showing another embodiment of the ionizer.

FIG. 8 shows a modification example of the ionizer. An ionizer 119 shown there includes a lamp 133 and an EI device 134. The EI device 134 is used for the analyzer 3 of FIGS. 1, 6, and 7 in place of the EI device 34 shown in FIG. 3. The EI device 134 includes an external electrode 138a, an internal electrode 138b, a collector electrode 140, and a filament 137. Reference numerals 139a and 139b depict lead-in electrodes. An ionizing region is formed inside of the internal electrode 138b. The external electrode 138a is formed in a rectangular-parallelepiped box shape without a side surface on a lead-in electrode 139a side, that is, in a square column shape. The external electrode 138a has each side surface serving as a plate-shaped electrode. The external electrode 138a has a space inside, and the internal electrode 138b is provided in that space. The external electrode 138a has a pair of side surfaces facing each other on which sample introduction openings 141a and 141b are provided. Also, the external electrode 138a has another pair of side surfaces facing each other on which electron passage openings 142a and 142b are provided. Here, these openings 141a, 141b, 142a, and 142b may have a mesh therein. Also, the external electrode 138a may be cylindrical in shape.

The gas to be measured is introduced to the inside of the external electrode 138a, as indicated by an arrow E, via the sample introduction openings 141a and 141b. The gas introduced but not gasified is discharged to the outside via the sample introduction openings 141a and 141b. The gas may be introduced and discharged via the electron passage openings 142a and 142b.

The lamp 133 is disposed so that its light-emitting surface faces the sample introduction opening 141a. The ionizing region in the internal electrode 138b is irradiated with vacuum ultraviolet light emitted from the lamp 133 through the sample introduction opening 141a. The filament 137 is disposed so as to face the electron passage opening 142a. The collector electrode 140 is disposed so as to face the other electron passage opening 142b. Electrons discharged from the filament 137 pass through the electron passage opening 142a as indicated by an arrow F to be introduced into the ionizing region in the internal electrode 138b. Electrons passing through the ionizing region without providing an electron impact on gas molecules then pass through the electron passage opening 142b as indicated by an arrow G to be collected in the collector electrode 140.

Since the ionizer 119 according to the present modification example is configured as described above, in the same manner as the ionizer using the EI device 34 shown in (a) and (b) of FIG. 3, EI is performed by electrons emitted from the filament 137, and PI is performed by vacuum ultraviolet light emitted from the lamp 133. Also, the external electrode 138a is formed of a plate-shaped electrode in the EI device 134. Therefore, compared with the EI device 34 using a mesh-shaped electrode shown in (a) and (b) of FIG. 3, the area of the external electrode 138a can be increased, thereby increasing the amount of discharge of secondary electrons from the external electrode 138a by irradiation of the vacuum ultraviolet light.

Fourth Embodiment of the Gas Analyzer

Figure 12:
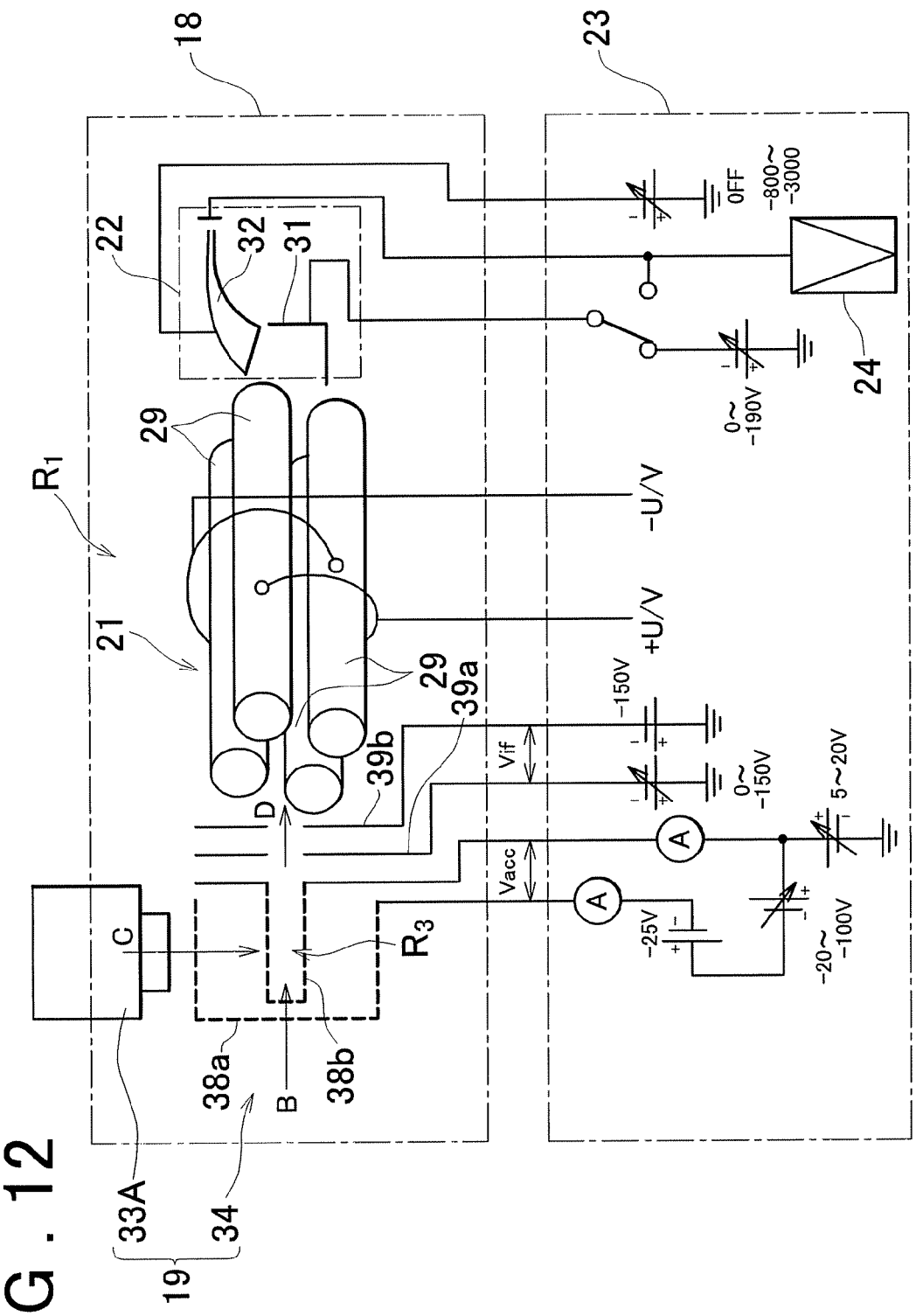
FIG. 12 is a view showing still another embodiment of the gas analyzer according to the present invention.

FIG. 12 shows still another embodiment of the gas analyzer according to the present invention. A gas analyzer shown there is constructed by modifying the embodiment shown in FIG. 2. Specifically, the filaments 37a, the filaments 37b, and their accompanying electric circuits are removed from the gas analyzer shown in FIG. 2. That is, the present embodiment excludes the filaments 37a and 37b serving as the electron generating means that generates electrons due to current application, and also as secondary electron generating means that generates secondary electrons due to light irradiation from the lamp 33A.

In the present embodiment, when a measurement based on the ionization using EI method is performed, a potential state between the external electrode 38a (V2) and the internal electrode 38b (V1) is set as Vacc=V2−V1<0. Then, the lamp 33A emits light, which strikes the external electrode 38a, the internal electrode 38b and, other structures as the case may be, to generate secondary electrons from them. The secondary electrons thus generated are accelerated by Vacc<0 to travel the ionizing region R3, and the accelerated electrons collide with gas molecules in the ionizing region R3 to ionize the gas components. Upon electron ionization, fragment ions are generated together with parent ions. If the energy of the secondary electrons is small, the amount of generated fragment ions is small, and therefore the intensity of the parent ions is strong. If the energy of the secondary electrons is large, the amount of generated fragment ions is large, and therefore the intensity of the parent ions is weak.

On the other hand, when a measurement based on the ionization using PI method is performed, a potential state between the external electrode 38a (V2) and the internal electrode 38b (V1) is set as Vacc=V2−V1=0 or Vacc=V2−V1>0. Then, the lamp 33A emits light, which strikes gas molecules in the ionizing region R3 to ionize them. At this time, light also strikes the external electrode 38a, the internal electrode 38b and other structures as the case may be, to thereby generate secondary electrons from them. However, the generated secondary electrons are not accelerated due to Vacc=0, or are accelerated with Vacc>0 in a direction away from the ionizing region R3 so as to be prevented or suppressed from traveling the ionizing region R3. Therefore, even if secondary electrons are generated, electron ionization does not occur, and only photo-ionization is performed. By virtue of ionization only by photo-ionization, information only about the parent ions without containing fragment ions can be obtained.

Other Embodiments

While the present invention has been described with reference to the preferred embodiments, the present invention is not limited to these embodiments, and can be variously modified within the scope of the invention described in the claims.

For example, in the embodiment of FIG. 1, the sample chamber R0 is formed of the temperature programmed desorption analyzer 2. In the embodiment of FIG. 6, the sample chamber R0 is formed of the TG-DTA device 52. However, the sample chamber R0 can also be formed of any other thermal treatment device. Furthermore, although the quadrupole filter 21 is exemplified as ion separating means in the embodiment of FIG. 1, any ion separator based on other principle can be used.

Figure 4:
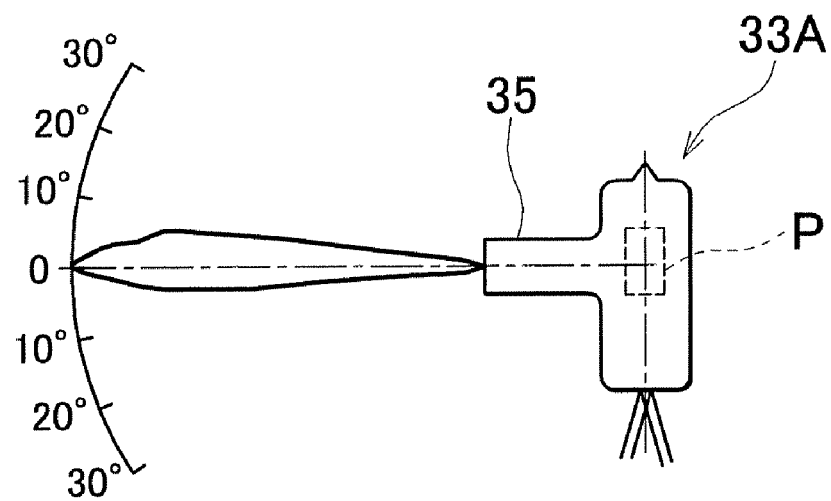
FIG. 4 is a view showing a light discharge angle of a lamp for use in PI.
Figure 4:
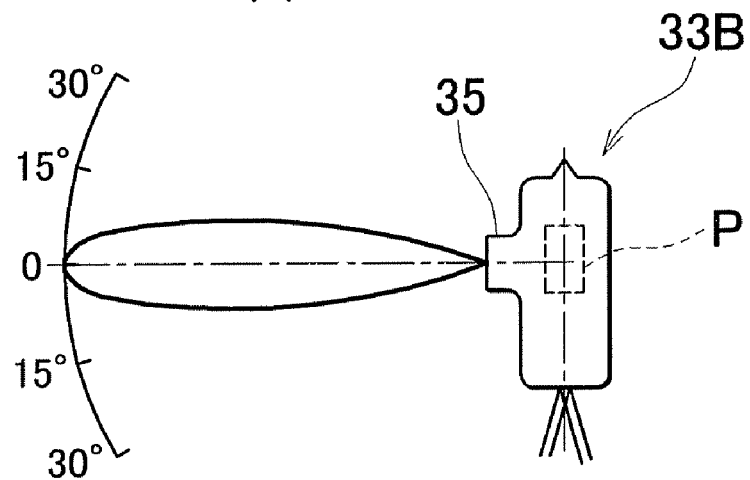

In the embodiment of FIG. 1, the lamp 33A shown in (a) of FIG. 4 is used as the PI lamp 33A. Alternatively, a lamp 33B shown in (b) of FIG. 4 can be used. Even when this lamp 33B was used, the ion intensity of the generated gas could be obtained. In other words, the gas could be sufficiently ionized based on PI using the lamp 33B.

The PI lamp 33A has a long cylinder 35 from a light-emitting source P, and an angle of divergence of emission light is suppressed about 10 degrees on one side and 20 degrees on both sides in a vertical direction. By contrast, the cylinder 35 of the lamp 33B is short, and an angle of divergence of emission light is relatively wide, specifically, about 17 degrees on one side and 34 degrees on both sides in a vertical direction. In such a manner, by changing the length of the cylinder 35, the angle of divergence of emission light can be adjusted.

Next, in the embodiment of FIG. 1, one type of PI lamp 33A is provided in the ionizer 19. However, the number of lamps can be two or more. Also in such a case, the plurality of lamps desirably discharge light beams of different wavelengths. Then, light having a desired energy amount can be selected to ionize the gas.

In the above embodiments, the external electrode 38a, the internal electrode 38b, and the filaments 37a and 37b of FIG. 2 are exemplified as secondary electron generating means that generates secondary electrons by being applied with light emitted from the lamp 33A or the like which are the light emitting means. However, the secondary electron generating means is not limited to an element that is activated by current application, and may be a simple metal member which is not supposed to receive current application. For example, when a casing containing the external electrode 38a, the internal electrode 38b, and the filaments 37a and 37b is employed, the casing may be the secondary electron generating means.

EXAMPLE 1

In the gas analyzer 1 of FIG. 1,
(1) a mixed solution of toluene and isopropyl alcohol is disposed at a predetermined position in the sample chamber R0 as a sample S,
(2) a He (helium) gas is introduced as a carrier gas,
(3) vacuum ultraviolet light spreading as shown in FIG. 4(a) and having energy of 10.2 eV is supplied from the PI lamp 33A of FIG. 2 to the ionizing region R3 in front of the gas outlet opening of the gas conveyor 4,
(4) electric current is not applied to the filaments 37a and 37b of FIG. 2 (that is, no electrons are generated), and
(5) between the external electrode 38a and the internal electrode 38b, three types of voltage, that is, −15V, 0V, and +15V, are applied as an electron acceleration voltage Vacc.
  Here, a − (minus) potential in the electron acceleration voltage Vacc has a polarity of accelerating the secondary electrons generated by vacuum ultraviolet light in FIG. 2 in a direction toward the internal electrode 38b from the external electrode 38a. A + (plus) potential has a polarity of accelerating the secondary electrons generated by vacuum ultraviolet light in FIG. 2 in a direction toward the external electrode 38a from the internal electrode 38b.

Figure 9:
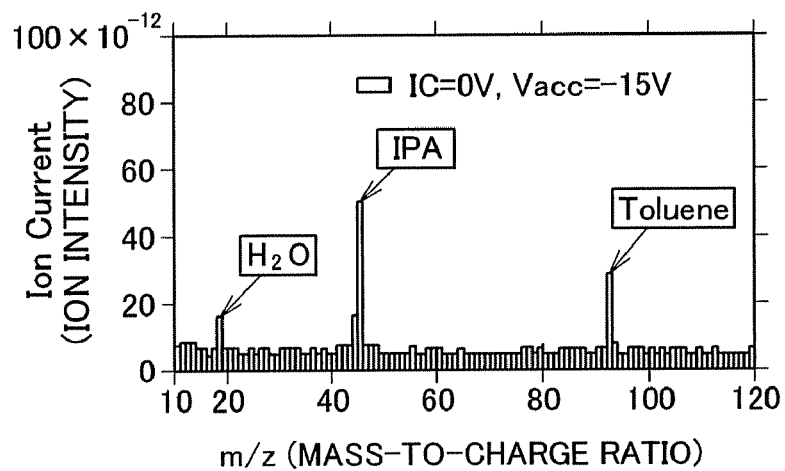
FIG. 9 is a view showing graphs of the results obtained from experiments by using the gas analyzer according to the present invention.
Figure 9:
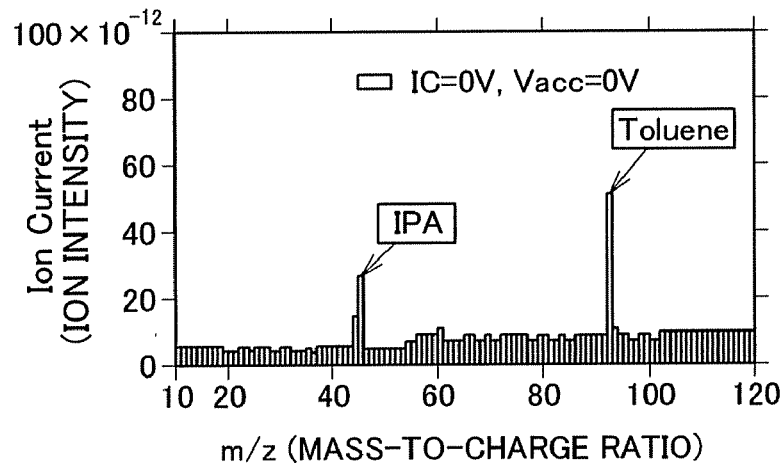
Figure 9:
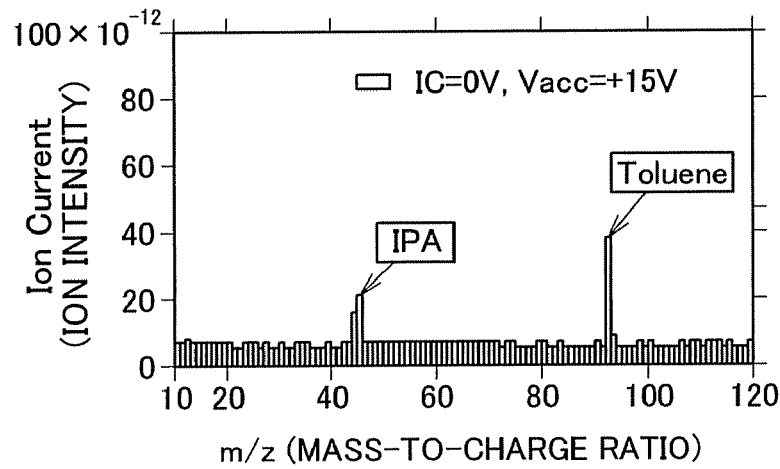

Under the above conditions, while the temperature of the sample S of FIG. 1 was gradually increased, the ion intensity of the gas generated from the sample S was measured. Upon displaying the measurement results on the screen of the display, images shown in FIG. 9 was obtained. (a) of FIG. 9 shows measurement results when the electron acceleration voltage Vacc=−15V, (b) of FIG. 9 shows measurement results when the electron acceleration voltage Vacc=0V, and (c) of FIG. 9 shows measurement results when the electron acceleration voltage Vacc=+15V.

From these experiments, the following can be found. When the electron acceleration voltage was minus ((a) of FIG. 9), we could a signal corresponding to a mass-to-charge ratio (m/e)=18 that seemed to represent $H_2O$, whose molecules are not ionized by vacuum ultraviolet light of 10.2 eV. This indicates that if the electron acceleration voltage is (minus), EI occurs even when no electrons are generated from the filaments. Also, as can be seen from (b) of FIG. 9 and (c) of FIG. 9, if the electron acceleration voltage is 0 (zero) or + (plus), ionization based on only PI was performed without EI.

EXAMPLE 2

In the gas analyzer 1 of FIG. 1,
(1) toluene, which is a volatile organic solvent is disposed at a predetermined position in the sample chamber R0 as a sample S,
(2) a He (helium) gas is introduced as a carrier gas,
(3) vacuum ultraviolet light spreading as shown in (a) of FIG. 4 and having energy of 10.2 eV is supplied from the PI lamp 33A of FIG. 2 to the ionizing region R3 in front of the gas outlet opening of the gas conveyor 4,
(4) electric current is not applied to the filaments 37a and 37b of FIG. 2 (that is, no electrons are generated), and
(5) no electron acceleration voltage Vacc is applied between the external electrode 38a and the internal electrode 38b (Vacc=0).

Under the above conditions, the ion intensity of the gas generated from the sample S was measured without increasing the temperature of the sample S (note that toluene generates gas even if its temperature is not increased). In the present example, it seems that light emitted from the PI lamp 33A collides with the structures, such as the electrode 38a, etc., to generate secondary electrons from these structures. However, since the electron acceleration voltage Vacc is not applied, EI may not occur. Upon displaying the measurement results on the screen of the display, an image shown in (a) of FIG. 10 was obtained.

Figure 10:
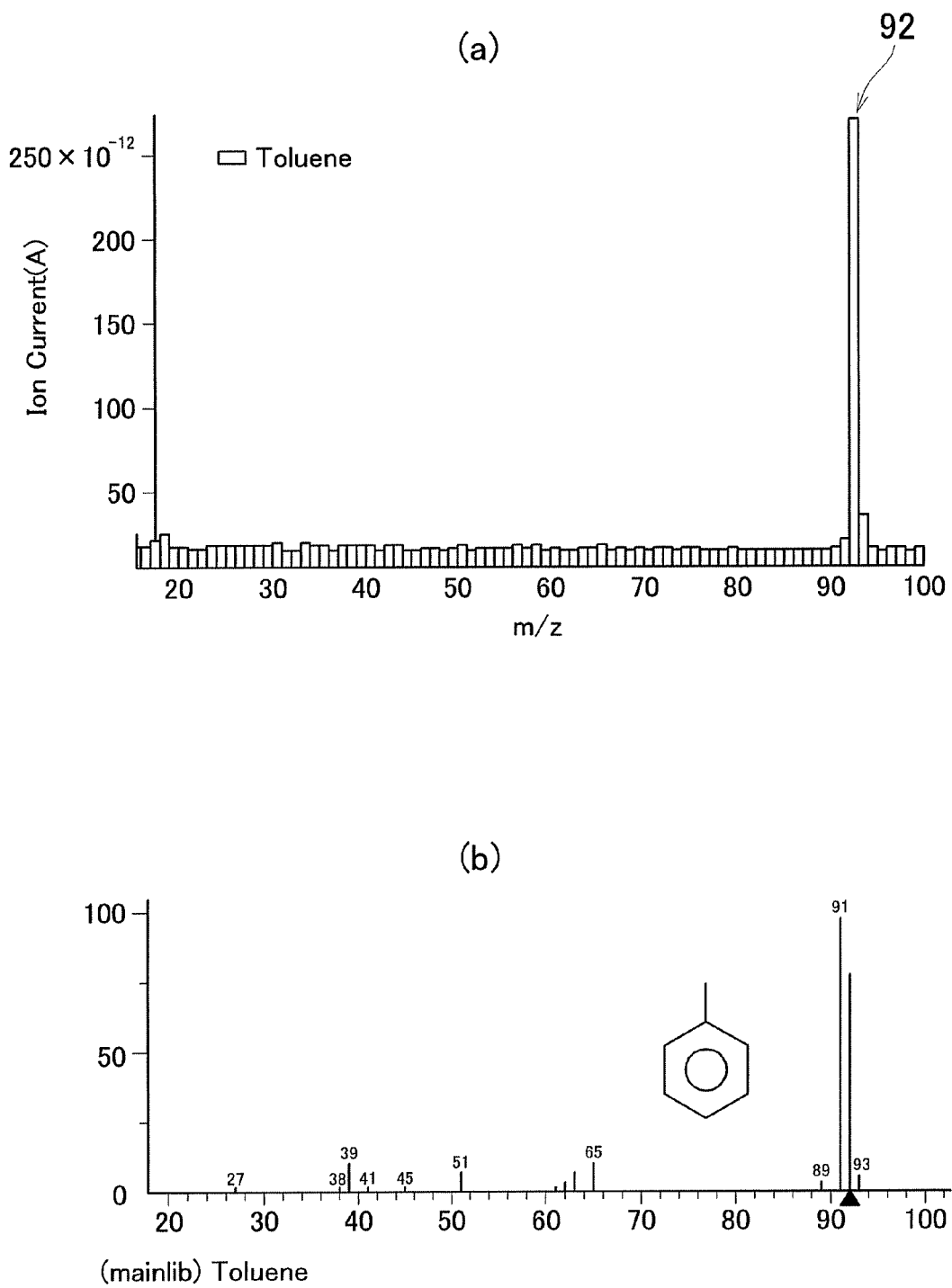
FIG. 10 is a view showing graphs of the results obtained from another experiments by using the gas analyzer according to the present invention.

(b) of FIG. 10 shows library data corresponding to the measurement based on the EI method. Specifically, the mass spectrum of (b) of FIG. 10 correspond to the measurement results obtained under conditions such that, in FIG. 2, (1) the PI lamp 33A is put out to be set at OFF, (2) the filaments 37a and 37b are electrically energized to generate electrons, and (3) an electron acceleration voltage with a predetermined value for accelerating the electrons in a direction toward the internal electrode 38b from the external bulb 38a.

From these experiments, the following can be found. In the mass spectrum of (a) of FIG. 10, a mass number of 92 represents a parent ion. Then, since fragment ions cannot be observed in (a) of FIG. 10, it can be found that the sample has been ionized by only PI.

EXAMPLE 3

The present inventors conducted the same generated gas analysis as that in Example 2 on materials of hexane, benzene, acetone, xylene, and ethanol, which are organic solvents other than toluene. As a result, it was found that with the PI lamp 33A being put on to be set ON and with the electron acceleration voltage Vacc being not applied or being set in a + potential state (Vacc>0), only parent ions are generated and no fragment ions are generated.

EXAMPLE 4

In the gas analyzer 1 of FIG. 1, two samples of polymethyl methacrylate were prepared as samples S, and these were separately disposed at predetermined positions in the sample chamber R0 to separately perform a measurement based on the EI method and a measurement based on the PI method under the same measurement conditions.

A measurement based on the EI method was performed under the following conditions:
(1) the PI lamp 33A of FIG. 2 is put out to be set at OFF not to perform PT;
(2) the filament 37a or 37b is electrically energized to be set at ON to generate electrons; and
(3) a minus electron acceleration voltage (Vacc<0) is applied to the electrodes 38a and 38b.

Also, a measurement based on the PI method was performed under the following conditions:
(1) the PI lamp of FIG. 2 is supplied with current to be set at ON to emit light toward the gas;
(2) the filaments 37a and 37b are put out to be set at OFF to stop generating electrons; and
(3) the electron acceleration voltage between the electrodes 38a and 38b is set as Vacc=0.

Figure 11:
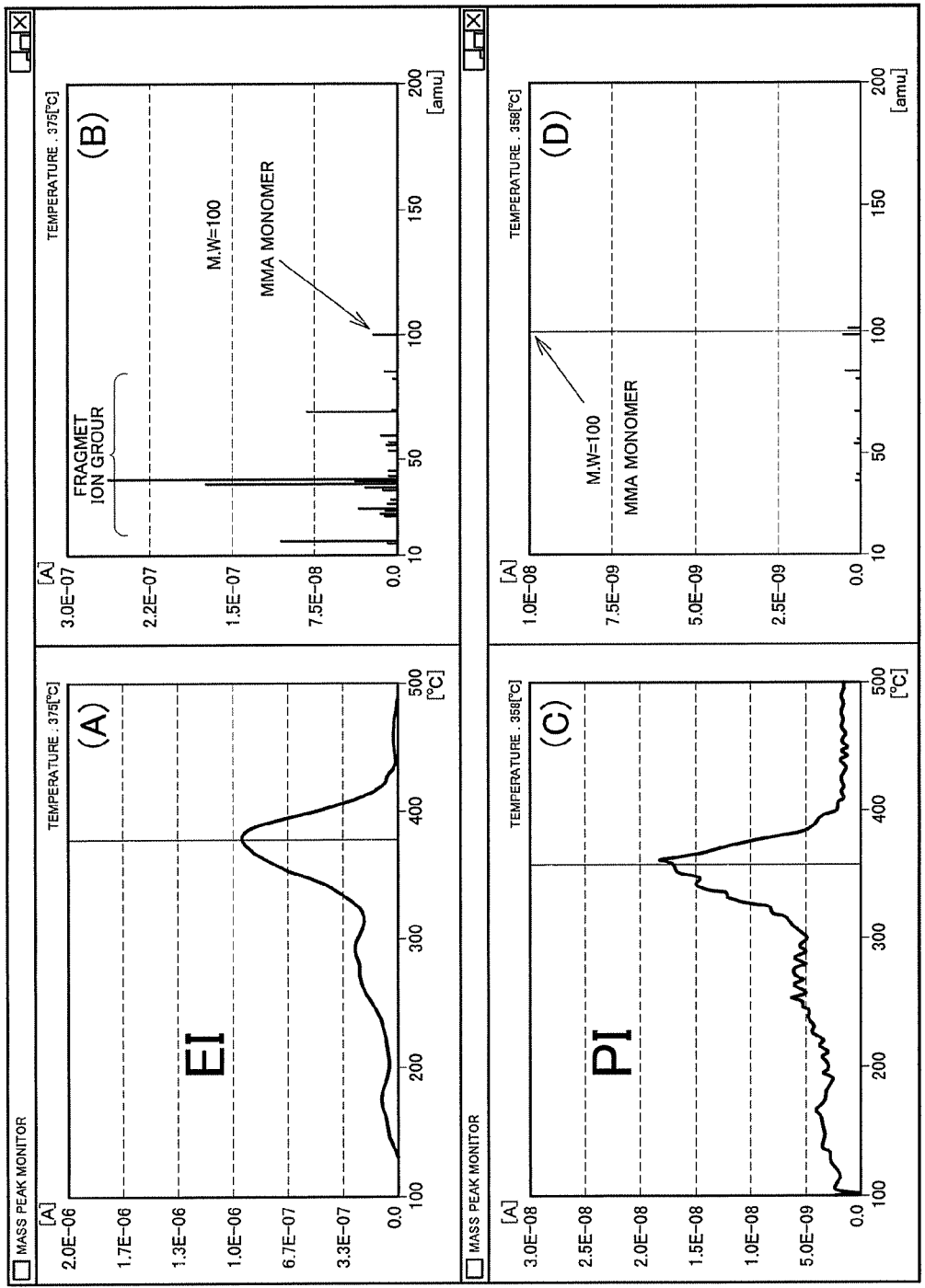
FIG. 11 is a view showing another example of image displays of measurement results obtained by using the gas analyzer according to the present invention.

Under the above conditions, while the temperature of the sample S was gradually increased, the ion intensity of the gas generated from the samples S was measured. Upon displaying the measurement results on the screen of the display, an image shown in FIG. 11 was obtained. FIG. 11(A) is a graph of a total ion intensity chart obtained as the measurement results based on only the EI method, FIG. 11(B) is a graph of the mass spectrum obtained as the measurement results based on only the EI method. Also, FIG. 11(C) is a graph of a total ion intensity chart obtained as the measurement results based on only the PI method, FIG. 11(D) is a graph of the mass spectrum obtained as the measurement results based on only the PI method.

From these experiments, the following can be found. As can be seen from the mass spectrum of FIG. 11(D), with PI using the PI lamp 33A (that is, vacuum ultraviolet light traveling as spreading), the gas could be sufficiently ionized. Also, the mass spectrum of FIG. 11(D) is based on PI, and the obtained peak is a peak of methyl methacrylate (MMA), which is a generated gas, and a peak of parent ions. The mass spectrum in FIG. 11(B) is based on EI, and it can be found that fragment ions are contained. Furthermore, since the intensity of the parent ions with the mass-to-charge ratio (m/e)=100 is extremely low, it can be understood that fragment occurs in large degree.

INDUSTRIAL APPLICABILITY

The gas analyzer according to the present invention is suitable for the purpose in which when a gas containing a plurality of molecular components is generated from a sample, these plurality of molecular components are ionized almost simultaneously within a short period of time for analysis. That is, the gas analyzer can be applied to the purpose of measuring a gas generated from a sample in real-time.

The invention claimed is:
1. A gas analyzer comprising:
light emitting means that emits light having a light directivity lower than that of laser light toward an ionizing region;

electron generating means that is electrically energized to generate electrons traveling toward the ionizing region;

ion separating means that separates, according to a mass-to-charge ratio, ions of a gas ionized by the light emitting means; and ion detecting means that detects the ions separated by the ion separating means;

wherein both the light emitting means and the electron generating means are mounted around the ionizing region, and wherein emitting light from the light emitting means and generating electrons from the electron generating means can be selectively performed.

2. The gas analyzer according to claim 1, wherein the electron generating means
comprises:
secondary electron generating means that is irradiated with light emitted from the light emitting means to generate secondary electrons traveling toward the ionizing region.

3. The gas analyzer according to claim 1, comprising electrodes that can take a potential state of accelerating electrons in a direction away from the ionizing region or a zero-potential state.

4. The gas analyzer according to claim 3, comprising electrodes that can take a potential state of accelerating electrons toward the ionizing region.

5. The gas analyzer according to claim 4, wherein the electron generating means and the electrodes are capable of allowing light path through.

6. The gas analyzer according to claim 5, wherein the electron generating means is a filament formed of a wire element, and
the electrodes include a combination of two electrodes selected from a mesh-shaped electrode, a spiral-shaped electrode, and a plate-shaped electrode partially provided with an opening capable of transmitting light.

7. The gas analyzer according to claim 6, wherein the light emitting means emits ultraviolet light or vacuum ultraviolet light.

8. The gas analyzer according to claim 7, wherein the light emitting means is a discharge tube formed with a gas sealed therein, and the gas is a deuterium gas, a krypton gas, or an argon gas.

9. The gas analyzer according to claim 8, further comprising:
an analysis chamber that contains a light emitting port of the light emitting means, the ion separating means, and an ion receiving port of the ion detecting means;
a sample chamber where a sample is placed; and
gas conveying means provided between the sample chamber and the analysis chamber to convey a gas generated from the sample to the analysis chamber.

10. The gas analyzer according to claim 9, further comprising heating means that heats the sample.

11. The gas analyzer according to claim 10, wherein
the sample chamber is at a high pressure inside, and the analysis chamber is at a low pressure inside, and
the gas conveying means includes:
an inner tube that conveys the gas;
an outer tuber that covers the inner tube; and
pressure adjusting means that sets a pressure of an intermediate chamber formed by the inner tube and the outer tube at a pressure lower than the pressure inside the sample chamber and higher than a pressure inside the analysis chamber.

12. The gas analyzer according to claim 11, wherein the inner tube and the outer tube each have an orifice at an end on a side of the sample and have an opening at an end on a side of the ionizing means.

13. The gas analyzer according to claim 12, wherein a member that throttles down a cross-sectional area of a gas flow in a direction looking from the sample chamber to the analysis chamber.

14. The gas analyzer according to claim 13, wherein
the pressure adjusting means includes an exhaust pump that exhausts air from the intermediate chamber and a flow-rate adjuster provided in front of the exhaust pump.

15. The gas analyzer according to claim 14, further comprising, in addition to the light emitting means, another light emitting means that emits light having a different wavelength to the light emitting means, wherein
the gas in the ionizing region is ionized with light emitted from the light emitting means or the other light emitting means.

16. The gas analyzer according to claim 4, comprising:
electrodes that accelerate the electrons; and
control means that controls operations of the light emitting means, the electron generating means, and the electrodes, wherein
the control means selectively performs a photo-ionization mode and an electron ionization mode,
the photo-ionization mode having a condition in which,
the light emitting means is set to be in a state where light is emitted,
the electron generating means is set to be in a potential state where no electron is generated, and
the electrodes are set to be in a zero potential state or a potential state of accelerating the electrons in a direction away from the ionizing region, and
the electron ionization mode having a condition in which,
the light emitting means is set to be in a state where light is not emitted,
the electron generating means is set to be in a potential state of generating electrons, and
the electrodes are set to be in a potential state of accelerating the electrons toward the ionizing region.

17. The gas analyzer according to claim 4, comprising:
electrodes that accelerate the electrons; and
control means that controls operations of the light emitting means, the electron generating means, and the electrode, wherein
the control means selectively performs a photo-ionization mode, an electron ionization mode, and a photo-electron ionization mode,
the photo-ionization mode having a condition in which,
the light emitting means is set to be in a state where light is emitted,
the electron generating means is set to be in a potential state where no electron is generated, and
the electrodes are set to be in a zero potential state or a potential state of accelerating the electrons in a direction away from the ionizing region,
the electron ionization mode having a condition in which,
the light emitting means is set to be in a state where light is not emitted,
the electron generating means is set to be in a potential state of generating electrons, and
the electrodes are set to be in a potential state of accelerating the electrons toward the ionizing region, and the photo-electron ionization mode having a condition in which,
the light emitting means is set to be in a state where light is emitted,
the electron generating means is set to be in a potential state where no electron is generated, and
the electrodes are set to be in a potential state of accelerating the electrons toward the ionizing region.

18. The gas analyzer according to claim 4, comprising:
electrodes that accelerate the electrons; and
control means that controls operations of the light emitting means, the electron generating means, and the electrode, wherein
the control means selectively performs a photo-ionization mode and a photo-electron ionization mode,
the photo-ionization mode having a condition in which,
the light emitting means is set to be in a state where light is emitted,
the electron generating means is set to be in a potential state where no electron is generated, and
the electrodes are set to be in a zero potential state or a potential state of accelerating the electrons in a direction away from the ionizing region, and
the photo-electron ionization mode having a condition in which,
the light emitting means is set to be in a state where light is emitted,
the electron generating means is set to be in a potential state where no electron is generated, and
the electrodes are set to be in a potential state of accelerating the electrons toward the ionizing region.

19. The gas analyzer according to claim 18, further comprising
arithmetic operating means that arithmetically produce the intensity of an ion based on an output signal of the ion detecting means, wherein
the arithmetic operating means performs an arithmetic operation of taking a difference of an output signal of the ion detecting means in the photo-ionization mode from an output signal of the ion detecting means in the photo-electron ionization mode.

20. The gas analyzer according to claim 4, comprising:
electrodes that accelerate the electrons; and
control means that controls operations of the light emitting means, the electron generating means, and the electrode, wherein
the control means selectively performs an electron ionization mode and a photo-electron ionization mode,
the electron ionization mode having a condition in which,
the light emitting means is set to be in a state where light is not emitted,
the electron generating means is set to be in a potential state of generating electrons, and
the electrodes are set to be in a potential state of accelerating the electrons toward the ionizing region, and
the photo-electron ionization mode having a condition in which,
the light emitting means is set to be in a state where light is emitted,
the electron generating means is set to be in a potential state where no electron is generated, and
the electrodes are set to be in a potential state of accelerating the electrons toward the ionizing region.

21. The gas analyzer according to claim 20, further comprising
arithmetic operating means that arithmetically produce the intensity of an ion based on an output signal of the ion detecting means, wherein
the arithmetic operating means performs an arithmetic operation of taking a difference of an output signal of the ion detecting means in the electron-ionization mode from an output signal of the ion detecting means in the photo-electron ionization mode.

* * * * *